(12) United States Patent
Hayashida et al.

(10) Patent No.: US 11,141,215 B2
(45) Date of Patent: Oct. 12, 2021

(54) ENERGY TREATMENT INSTRUMENT, TREATMENT SYSTEM, AND CONTROLLER

(71) Applicant: OLYMPUS CORPORATION, Hachioji (JP)

(72) Inventors: Tsuyoshi Hayashida, Hachioji (JP); Satomi Sakao, Hachioji (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 374 days.

(21) Appl. No.: 15/907,712

(22) Filed: Feb. 28, 2018

(65) Prior Publication Data
US 2018/0185089 A1 Jul. 5, 2018

Related U.S. Application Data

(63) Continuation of application No. PCT/JP2016/063097, filed on Apr. 26, 2016.

(51) Int. Cl.
*A61B 18/14* (2006.01)
*A61B 18/12* (2006.01)
*A61B 18/00* (2006.01)

(52) U.S. Cl.
CPC ...... *A61B 18/1447* (2013.01); *A61B 18/1206* (2013.01); *A61B 18/1445* (2013.01);
(Continued)

(58) Field of Classification Search
CPC ...... A61B 18/1445; A61B 2018/00589; A61B 2018/00875; A61B 2018/00904;
(Continued)

(56) References Cited

U.S. PATENT DOCUMENTS

| 5,370,659 A | 12/1994 | Sakashita |
| 2004/0243125 A1 | 12/2004 | Dycus et al. |

(Continued)

FOREIGN PATENT DOCUMENTS

| CN | 105246422 A | 1/2016 |
| EP | 3000425 A1 | 3/2016 |

(Continued)

OTHER PUBLICATIONS

Phil Johnson and Shaun Roberts, "Resistance and thickness of wire (cross-sectional area)", 2005, Durham University, https://community.dur.ac.uk/p.m.johnson/electric_circuits/08_resistance_thickness.htm (Year: 2005).*

(Continued)

*Primary Examiner* — Linda C Dvorak
*Assistant Examiner* — Nils A Potter
(74) *Attorney, Agent, or Firm* — Oliff PLC

(57) ABSTRACT

An energy treatment instrument includes a first grasping piece, and a second grasping piece which opens or closes relative to the first grasping piece and which grasps a blood vessel between the first grasping piece and the second grasping piece. In accordance with the kind of blood vessel grasped between the first grasping piece and the second grasping piece, an actuation state of the energy treatment instrument is switched between a first mode to coagulate a blood vessel of a circulatory system, and a second mode to coagulate a blood vessel of a pulmonary circulation in contrast to the first mode.

6 Claims, 12 Drawing Sheets

(52) U.S. Cl.
CPC ............... *A61B 2018/0066* (2013.01); *A61B 2018/00404* (2013.01); *A61B 2018/00589* (2013.01); *A61B 2018/00642* (2013.01); *A61B 2018/00702* (2013.01); *A61B 2018/00708* (2013.01); *A61B 2018/00875* (2013.01); *A61B 2018/00904* (2013.01)

(58) Field of Classification Search
CPC ...... A61B 2018/00708; A61B 18/1447; A61B 2018/00702; A61B 2018/0066; A61B 2018/00642
USPC .......................................................... 606/51
See application file for complete search history.

(56) References Cited

U.S. PATENT DOCUMENTS

| | | | |
|---|---|---|---|
| 2005/0113827 | A1 | 5/2005 | Dumbauld et al. |
| 2008/0009860 | A1 | 1/2008 | Odom |
| 2008/0039836 | A1 | 2/2008 | Odom et al. |
| 2008/0208108 | A1* | 8/2008 | Kimura ............... A61B 18/1206 604/22 |
| 2009/0138003 | A1 | 5/2009 | Deville et al. |
| 2009/0248003 | A1 | 10/2009 | Orszulak |
| 2009/0261804 | A1 | 10/2009 | McKenna et al. |
| 2011/0077629 | A1* | 3/2011 | Tanaka ................. A61B 18/085 606/28 |
| 2011/0118736 | A1 | 5/2011 | Harper et al. |
| 2011/0160725 | A1 | 6/2011 | Kabaya et al. |
| 2012/0022389 | A1* | 1/2012 | Sanders ............. A61B 17/0401 600/533 |
| 2012/0184990 | A1 | 7/2012 | Twomey |
| 2014/0066911 | A1 | 3/2014 | Nau, Jr. |
| 2014/0073900 | A1* | 3/2014 | Wood ................... A61B 5/0095 600/407 |
| 2014/0371527 | A1 | 12/2014 | Sato |
| 2015/0314134 | A1 | 11/2015 | Nowicki |
| 2016/0256071 | A1 | 9/2016 | Shelton, IV et al. |
| 2017/0238991 | A1* | 8/2017 | Worrell ................. H05K 3/061 |

FOREIGN PATENT DOCUMENTS

| | | |
|---|---|---|
| EP | 3417819 A1 | 12/2018 |
| EP | 3417820 A1 | 12/2018 |
| JP | 2005-512606 A | 5/2005 |
| JP | 2005-349022 A | 12/2005 |
| JP | 2008-036441 A | 2/2008 |
| JP | 2011-504794 A | 2/2011 |
| JP | 2011-104376 A | 6/2011 |
| JP | 2011-206554 A | 10/2011 |
| JP | 2014-195648 A | 10/2014 |
| JP | 2015-000093 A | 1/2015 |
| WO | 2011/052349 A1 | 5/2011 |
| WO | 2012/061638 A1 | 5/2012 |

OTHER PUBLICATIONS

Nathaniel G. dela Paz and Patricia A. D'Amore, "Arterial versus venous endothelial cells", 2008, PMC, vol. 335, pp. 5-16 ( Year: 2008).*
Aabbio, "Circulatory System: Facts, Function & Diseases", 2021, Aabbio, http://aabbiotech.com/Circulatory.html (Year: 2021).*
Gregory Trevors, Melissa Duffy, Roger Azevedo, "Note-taking within MetaTutor: interactions between an intelligent tutoring system and prior knowledge on note-taking and learning", 2014, Springer, vol. 62, pp. 507-528 (Year: 2014).*
Jun. 20, 2017 Office Action issued in Japanese Patent Application No. 2017-522572.
Mar. 21, 2019 Extended European Search Report issued in European Patent Application No. 16900403.3.
Jun. 14, 2016 International Search Report issued in Patent Application No. PCT/JP2016/063097.
Oct. 30, 2018 International Preliminary Report on Patentability issued in International Patent Application No. PCT/JP2016/063097.
Apr. 10, 2020 Office Action issued in Chinese Patent Application No. 201680058315.9.
Aug. 18, 2020 U.S. Office Action issued U.S. Appl. No. 15/998,411.
May 17, 2016 International Search Report issued in Patent Application No. PCT/JP2016/054309.
Aug. 21, 2018 International Preliminary Report on Patentability issued in International Application No. PCT/JP2016/054309.
Apr. 29, 2020 U.S. Office Action issued U.S. Appl. No. 15/998,411.
Jun. 1, 2020 Office Action issued in Chinese Patent Application No. 201680081862.9.
Jan. 22, 2021 Office Action issued in Chinese Patent Application No. 201880081862.9.

* cited by examiner

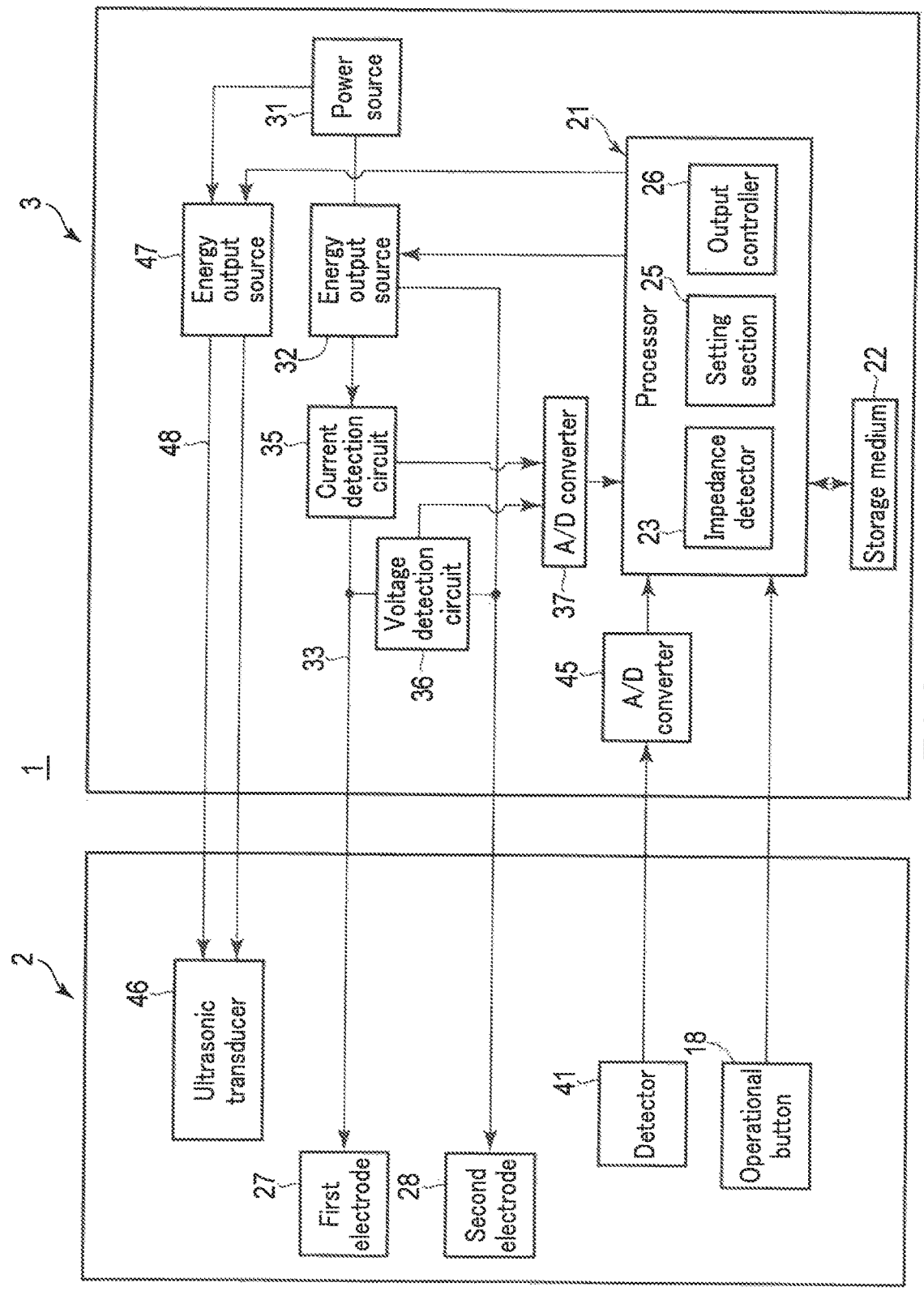
F I G. 2

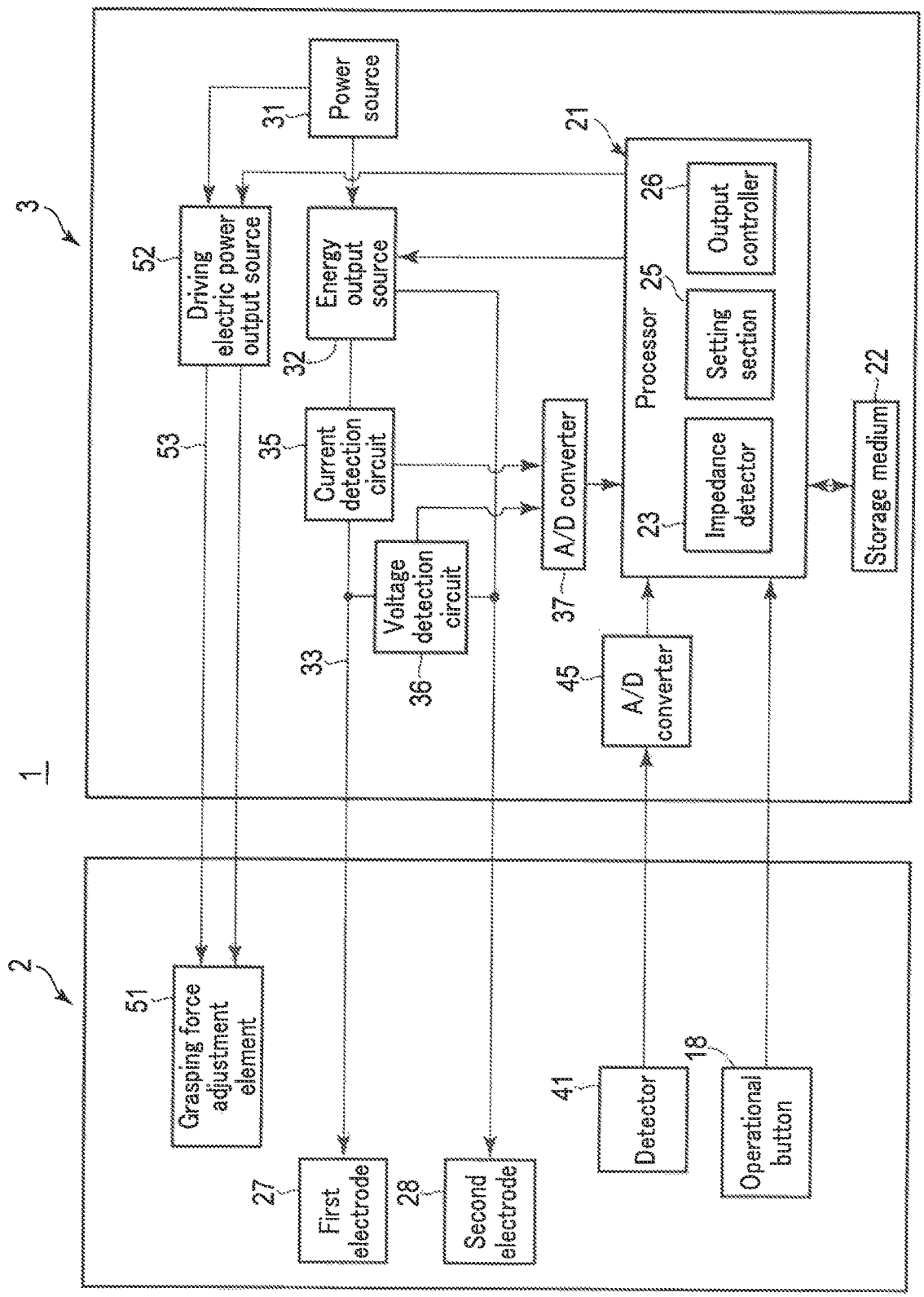
F I G. 12

ENERGY TREATMENT INSTRUMENT, TREATMENT SYSTEM, AND CONTROLLER

CROSS-REFERENCE TO RELATED APPLICATIONS

This is a Continuation Application of PCT Application No. PCT/JP2016/063097, filed Apr. 26, 2016, the entire contents of which are incorporated herein by reference.

BACKGROUND OF THE INVENTION

1. Field of the Invention

The present invention relates to an energy treatment instrument which applies treatment energy to a treated target grasped between a pair of grasping pieces, a treatment system comprising the energy treatment instrument, and a controller which is used together with the energy treatment instrument.

2. Description of the Related Art

International Publication No. 2012/061638 discloses an energy treatment instrument which grasps a treated target such as a living tissue between a pair of grasping pieces. In this energy treatment instrument, an electrode is provided in each of the grasping pieces. By the supply of electric energy to both of the electrodes, a high-frequency current flows between the electrodes through the grasped treated target. Thereby, the high-frequency current is applied to the treated target as treatment energy.

BRIEF SUMMARY OF THE INVENTION

According to one aspect of the invention, an energy treatment instrument including a first grasping piece, and a second grasping piece which opens or closes relative to the first grasping piece and which grasps a blood vessel between the first grasping piece and the second grasping piece, wherein in accordance with the kind of blood vessel grasped between the first grasping piece and the second grasping piece, an actuation state of the energy treatment instrument is switched between a first mode to coagulate a blood vessel of a circulatory system, and a second mode to coagulate a blood vessel of a pulmonary circulation in contrast to the first mode.

According to one another aspect of the invention, a controller which is used together with an energy treatment instrument, the energy treatment instrument comprising a first grasping piece, and a second grasping piece which opens or closes relative to the first grasping piece and which grasps a blood vessel between the first grasping piece and the second grasping piece, the controller including an energy output source which outputs electric energy that is supplied to the energy treatment instrument, and applies treatment energy to the blood vessel grasped. between the first grasping piece and the second grasping piece by the supply of the electric energy to the energy treatment instrument, and a processor which sets whether the grasped blood vessel is a blood vessel of a circulatory system or a blood vessel of a pulmonary circulation, the processor performing at least one of the following, controlling the output of the electric energy from the energy output source on the basis of the setting of the kind of grasped blood vessel, and making force of grasping the blood vessel between the first grasping piece and the second grasping piece greater when it is set that the grasped blood vessel is a blood vessel of the pulmonary circulation than when it is set that the blood vessel is a blood vessel of the circulatory system.

Advantages of the invention will be set forth in the description which follows, and in part will be obvious from the description, or may be learned by practice of the invention. The advantages of the invention may be realized. and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram showing a control configuration in the treatment system according to the first embodiment;

FIG. 12 is a block diagram showing a control configuration in a treatment system according to a second embodiment;

DETAILED DESCRIPTION OF THE INVENTION

First Embodiment

Figure 1:
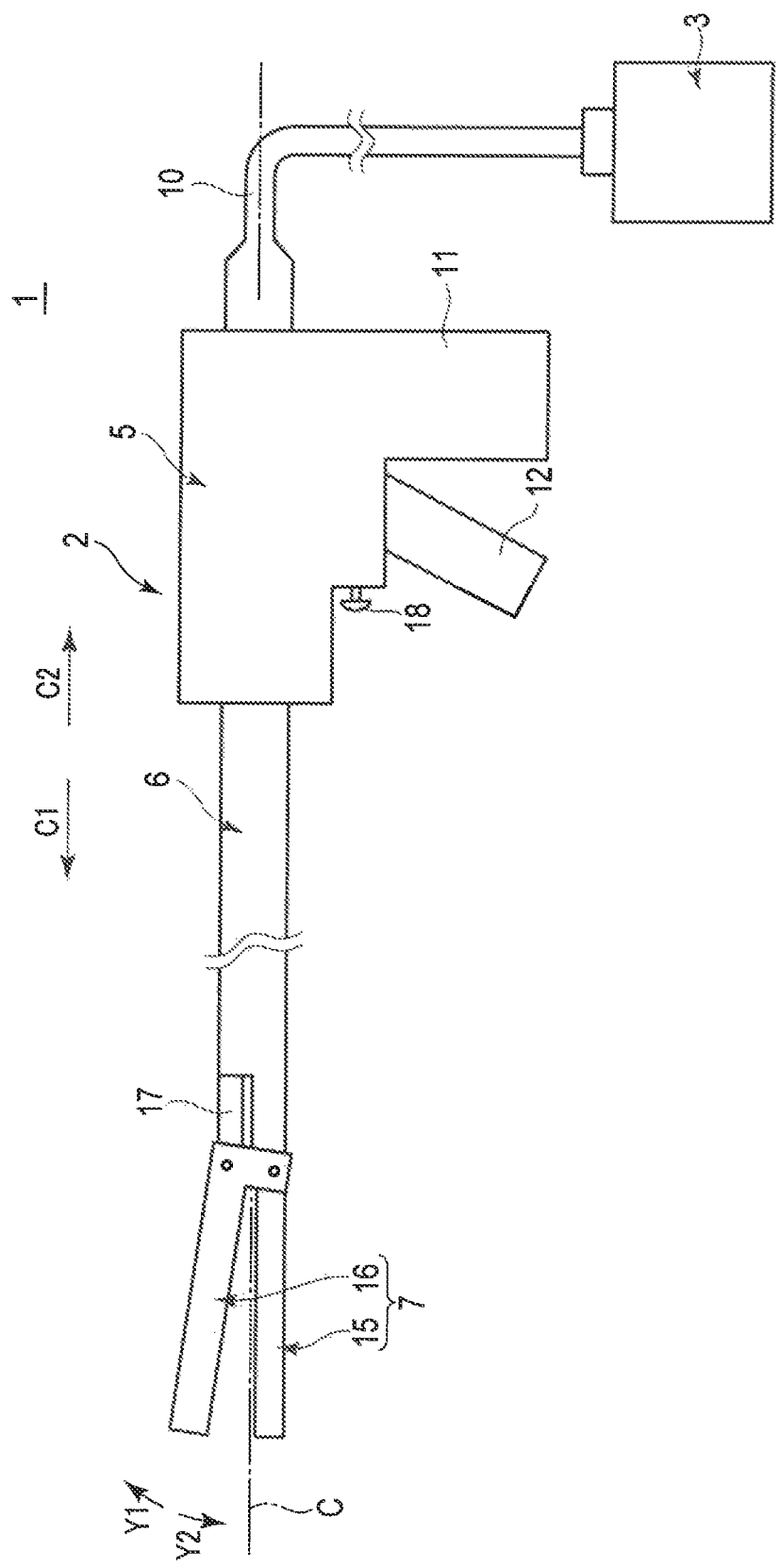
FIG. 1 is a schematic diagram showing a treatment system according to a first embodiment.

A first embodiment of the present invention. described with reference to FIG. 1 to FIG. 7. FIG. 1 is a diagram showing a treatment system 1 according to the present embodiment. As shown in FIG. 1, the treatment system 1 comprises an energy treatment instrument 2 and a controller (energy controller) 3. The energy treatment instrument 2 has a longitudinal axis C. Here, one side in a direction along the longitudinal axis C is a distal side (an arrow C1 side), and the side opposite to the distal side is a proximal side (an arrow C2 side).

The energy treatment instrument 2 comprises a housing 5 which is holdable, a sheath (shaft) 6 which is coupled to the distal side of the housing 5, and an end effector 7 provided in a distal portion of the sheath 6. One end of a cable 10 is connected to the housing 5 of the energy treatment instrument 2. The other end of the cable 10 is separably connected to the controller 3. Further, a grip (fixed handle) 11 is provided in the housing 5, and a handle (movable handle) 12 is revolvably attached to the housing 5. The handle 12 revolves relative to the housing 5, and the handle 12 opens or closes relative to the grip 11. Note that in the present embodiment, the handle 12 is located on the distal side of the grip 11, and moves substantially parallel to the longitudinal axis C in an operation of opening or closing relative to the grip 11, which is, however, not restrictive. For example, in a certain example, the handle 12 may be located on the proximal side of the rip 11 in another certain example, the handle 12 may be located on the side opposite to the grip 11 across the longitudinal axis C, and the movement direction of the handle 12 in the operation of opening or closing relative to the grip 11 may cross (may be substantially perpendicular to) the longitudinal axis C.

The sheath 6 extends along the longitudinal axis C. Further, the end effector 7 comprises a first grasping piece 15, and a second grasping piece 16 which opens or closes relative to the first grasping piece 15. The handle 12 and the end effector 7 are coupled to each other via a movable member 17 extending along the longitudinal axis C through the sheath 6. The handle 12 which is an open/close operation input section is opened or closed relative to the grip 11, whereby the movable member 17 moves relative to the sheath 6 and the housing 5 along the longitudinal axis C, and the pair of grasping pieces 15 and 16 open or close relative to each other. The grasping pieces 15 and 16 close relative to each other, and a living tissue such as a blood vessel is thereby grasped as a treated target between the grasping pieces 15 and 16. Open/close directions (directions of an arrow Y1 and an arrow Y2) of each of the grasping pieces 15 and 16 cross (are substantially perpendicular to) the longitudinal axis C.

Note that the end effector 7 has only to be configured so that the pair of grasping pieces 15 and 16 open or close relative to each other in response to each of the open and close operations of the handle 12. For example, in a certain example, one of the grasping pieces 15 and 16 is integral with the sheath 6 or fixed to the sheath 6, and the other of the grasping pieces 15 and 16 is revolvably attached to the distal portion of the sheath. 6. In another certain example, both of the grasping pieces 15 and 16 are revolvably attached to the distal portion of the sheath 6. In yet another certain example, a rod member (not shown.) is inserted through the sheath 6, and one of the grasping pieces 15 and 16 is formed by a portion of the rod member (probe) protruding toward the distal side from the sheath 6. Furth the other of the grasping pieces 15 and 16 is revolvably attached to the distal portion of the sheath 6. Moreover, in a certain example, a rotational operation knob (not shown) may be attached to the housing 5. In this case, the rotational operation knob is rotated around the longitudinal axis C relative to the housing 5, whereby the sheath 6 and the end effector 7 rotate around the longitudinal axis C relative to the housing 5 together with the rotational operation knob. Accordingly, the angular position of the end effector 7 around the longitudinal axis C is adjusted.

FIG. 2 is a diagram showing a control configuration in the treatment system 1. As shown in FIG. 2, the controller 3 comprises a processor (control section) 21 which controls the whole treatment system 1, and a storage medium 22. The processor 21 is formed from an integrated circuit including a central processing unit (CPU), an application specific integrated circuit (ASIC) or a field programmable gate array (FPGA), and the like. The processor 21 may be formed from one integrated circuit or may be formed from more than one integrated circuit. The processing in the processor 21 is performed in accordance with a program stored in the processor 21 or the storage medium 22. Further, a processing program for use in the processor 21, parameters and a table for use in the calculation in the processor 21, and others are stored in the storage medium 22. The processor 21 comprises an impedance detector 23, a setting section 25, and an output controller 26. The impedance detector 23, the setting section 25, and the output controller 26 function as parts of the processor 21, and perform parts of the processing performed by the processor 21.

In the end effector 7 of the energy treatment instrument 2, a first electrode 27 is provided in the first grasping piece 15, and a second electrode 28 is provided in the second grasping piece 16. The electrodes 27 and 28 are made of an electrically conductive material. The controller 3 comprises a power source 31 which is a battery, an outlet, or the like, and an energy output source (first energy output source) 32. The energy output source 32 electrically connected to the electrodes 27 and 28 via an electricity supply path (first electricity supply path) 33 extending through the cable 10. The energy output source 32 comprises a conversion circuit, an amplifier circuit, and others, and converts electric power from the power source 31. Then the energy output source 32 outputs electric energy (high-frequency electric power) resulting from the conversion. The electric energy output from the energy output source 32 is supplied to the electrodes 27 and 28 through the electricity supply path 33. The output controller 26 of the processor 21 controls driving of the energy output source 32, and controls the output of the electric energy from the energy output source 32. Thereby, one of output electric power P, an output current and an output voltage V in the energy output source 32 is adjusted, and the supply of the electric energy to the electrodes 27 and 28 is controlled.

The electric energy is supplied to the electrodes 27 and 28 from the energy output source 32 in a state where the treated target is grasped between the grasping pieces 15 and 16, whereby a high-frequency current flows between the electrodes 27 and 28 through the treated target grasped in contact with the electrodes 27 and 28. That is, the high-frequency current is applied to the treated target as treatment energy. The high-frequency current flows through the treated target, whereby heat is generated in the treated target, and the treated target is denatured by the heat. Accordingly, the treated target which is a blood vessel or the like is sealed (coagulated) by use of the high-frequency current. As described above, by the supply of the electric energy to the electrodes 27 and 28 of the energy treatment instrument 2 from the energy output source 32, the treatment energy (high-frequency current) is applied to the treated target grasped between the grasping pieces 15 and 16. Therefore, in the present embodiment, the grasping pieces 15 and 16 are an energy application section. which applies the high-frequency current to the grasped treated target. (blood vessel) as the treatment energy.

A current detection circuit 35 and a voltage detection circuit 36 are provided in the electricity supply path 33. In a state where the electric energy is output from the energy output source 32, the current detection circuit 35 detects the output current I, and the voltage detection circuit 36 detects the output voltage V. An A/D converter 37 is provided in the controller 3. An analog signal regarding the current I detected in the current detection circuit 35, and an analog signal regarding the voltage V detected in the voltage detection circuit 36 are transmitted to the A/D converter 37. The A/D converter 37 converts the analog signal regarding the current I and the analog signal regarding the voltage V into digital signals, and transmits the digital signals resulting from the conversion to the processor 21.

In a state where the electric energy is output from the energy output source 32, the processor 21 acquires information regarding the output current I and the output voltage V in the energy output source 32. Further, the impedance detector 23 of the processor 21 detects impedance of the electricity supply path 33 including the grasped treated target (blood vessel) and the electrodes 27 and 28 on the basis of the output current I and the output voltage V. Thereby, impedance Z between the pair of grasping pieces 15 and 16 (i.e., impedance of the grasped treated target) is detected.

As shown in FIG. 1, an operational button 18 is attached to the housing 5 as an energy operation input section. By the pressing of the operational button 18, an operation (signal) to output the electric energy to the energy treatment instrument 2 from the energy output source 32 is input to the controller 3. Note that a foot switch or the like separate from the energy treatment instrument 2 may be provided as the energy operation input section instead of or in addition to the operational button 18. As shown in FIG. 2, the processor 21 detects whether or not there is any operation input in the energy operation input section such as the operational button 18. The output controller 26 of the processor 21 controls the output of the electric energy from the energy output source 32 on the basis of the operation input with the operational button 18.

Figure 3:
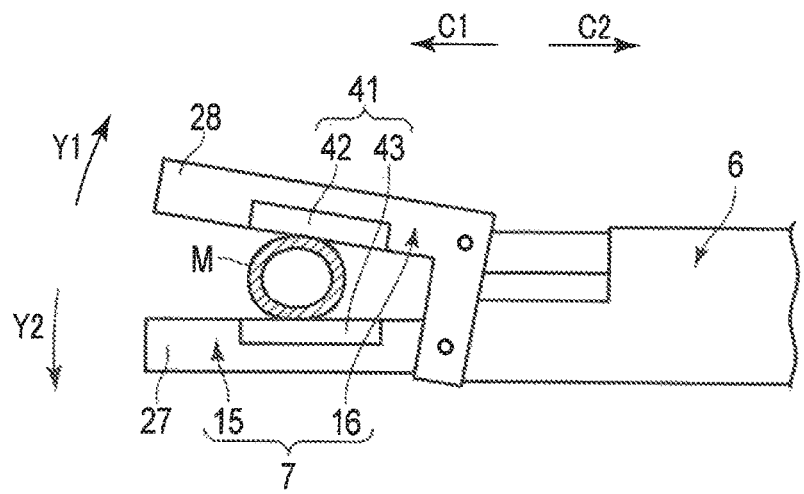
FIG. 3 is a schematic diagram showing a detector according to a certain example of the first embodiment.

Furthermore, a detector 41 is provided in the treatment system 1. The detector 41 detects a parameter regarding the kind of blood vessel grasped between the grasping pieces 15 and 16. FIG. 3 shows the detector 41 in a certain example. In the example shown in FIG. 3, the detector 41 comprises a light emitting element 42 and a light receiving element 43. The light emitting element 42 is provided in, for example, the second grasping piece 16, and emits two kinds of light different in wavelength toward the first grasping piece 15 in a state where a treated target such as a blood vessel M is grasper between the grasping pieces 15 and 16. For example, red light and infrared light are used as the two kinds of light emitted from the light emitting element 42. The light receiving element 13 is provided in, for example, the first grasping piece 15, and receives the light emitted from the light emitting element 42. In this instance, the quantity or the like of each of the two kinds of light received by the light receiving element 43 is detected as a parameter regarding the kind of grasped blood vessel M.

Note that the detector 41 is provided in the energy treatment instrument 2 in the present example, but the detector 41 may be provided separately from the energy treatment instrument 2.

As shown in FIG. 2, an A/D converter 45 is provided in the controller 3. An analog signal indicating the parameter regarding the kind of blood vessel detected by the detector 41 is transmitted to the A/D converter 45. The A/D converter 45 converts the analog signal indicating the parameter regarding the kind of blood vessel into a digital signal, and transmits the digital signal resulting from the conversion to the processor 21. Note that in a certain example, the A/D converter 45 may be provided in the detector 41. In this case, the analog signal indicating the parameter regarding the kind of blood vessel is converted into a digital signal in the detector 41, and the digital signal resulting from the conversion is transmitted from the detector 41 to the processor 21. Then the processor 21 calculates an oxygen concentration X of the grasped blood vessel on the basis of a detection result in the detector 41. In this instance, the ratio of the quantity of each of the two kinds of light to the total light quantity is calculated by use of the quantity of each of the two kinds of light detected by the light receiving element 43 of the first grasping piece 15. For example, a table or the like indicating the relation between the ratio of the quantity of each of the two kinds of light to the total light quantity and the oxygen concentration X of the grasped blood vessel is stored in the storage medium 22. Then the processor 21 calculates the oxygen concentration X of the grasped blood vessel on the basis of a detection result in the light receiving element 43 and the table stored in the storage medium 22.

The setting section 25 of the processor 21 judges whether or not the oxygen concentration X is higher than an oxygen concentration threshold Xth1. The oxygen. concentration threshold Xth1 may be set by the surgeon or the like, or may be stored in the storage medium 22. Further, the setting section 25 sets whether the grasped blood vessel is a blood vessel of a circulatory system or a blood vessel of a pulmonary circulation in accordance with the judgement result regarding the oxygen concentration X.

The output controller 26 of the processor 21 controls the output of the electric energy from the energy output source 32 on the basis of the detection result in the detector 41 and the setting of the kind of blood vessel. The actuation state of the energy treatment instrument 2 switches between a first mode (first actuation mode) and a second mode (second actuation mode) in response to the output state of the electric energy from the energy output source 32. In the present embodiment, the state of the application of the treatment energy (high-frequency current) to the grasped treated target (blood vessel) from the energy application section (the grasping pieces 15 and 16) varies between the first mode and the second mode.

Note that in a certain example, an ultrasonic transducer 46 may be provided in the energy treatment instrument 2 (inside the housing 5). In this case, the rod member is connected to the distal side of the ultrasonic transducer 46, and one of the grasping pieces 15 and 16 (e.g., the first grasping piece 15) is formed by a portion of the rod member protruding toward the distal side from the sheath 6. Moreover, in the present example, an energy output source (second energy output source) 47 is provided in the controller 3 in addition to the energy output source 32. The energy output source 47 is electrically connected to the ultrasonic transducer 46 via an electricity supply path (second electricity supply path) 48 extending through the cable 10. Here, the energy output source 47 may be integral with the energy output source 32, or may be formed separately from the energy output source 32.

In the present example, the energy output source 47 comprises a conversion circuit, an amplifier circuit, and others, and converts electric power from the power source 31. Then the energy output source 47 outputs electric energy (alternating-current electric power) resulting from the conversion. The electric energy output from the energy output source 47 is supplied to the ultrasonic transducer 46 through the electricity supply path 48. The output controller 26 of the processor 21 controls driving of the energy output source 47, and controls the output of the electric energy from the energy output source 47.

In the present example, the electric energy (alternating-current electric power) output from the energy output source 47 is supplied to be ultrasonic transducer 46, and ultrasonic vibration is thereby generated in the ultrasonic transducer 46. The generated ultrasonic vibration is transmitted to the distal side from the proximal side in the rod member (vibration transmitting member), and the rod member including one of the grasping pieces 15 and 16 (e.g., the first grasping piece 15) vibrates. The rod member vibrates in a state where the treated target is grasped between the grasping pieces 15 and 16, whereby the ultrasonic vibration is applied to the treated target as the treatment energy. In this instance, frictional heat resulting from the vibration is generated, and the treated target which is the blood vessel or the like can be cut open while being sealed. (coagulated) by the frictional heat.

In another certain example, a heater (not shown) may be provided in the end effector 7 (at least one of the grasping pieces 15 and 16) instead of the ultrasonic transducer 46. In this case, the electric energy (direct-current electric power or alternating-current electric power) output from the energy output source (47) is supplied to the heater through the electricity supply path (48). Thereby, heat is generated in the heater, and the treated target which is the blood vessel or the like can be cut open while being sealed (coagulated) by the heat generated in the heater. Even when each of the ultrasonic vibration and the heater heat or the like is applied to the grasped treated target (blood vessel) as the treatment. energy, at least one of the grasping pieces 15 and 16 functions as the energy application section which applies the treatment energy to the treated target (blood vessel).

Now, functions and advantageous effects according to the present embodiment are described. When conducting a treatment using the treatment system 1, a surgeon holds the housing 5 of the energy treatment instrument 2, and inserts the end effector 7 into a body cavity such as an abdominal cavity. Further, a blood vessel (treated target) is disposed between the grasping pieces 15 and 16, the handle 12 is closed relative to the grip 11, and the grasping pieces 15 and 16 are thereby closed relative to each other. Accordingly, the blood vessel is grasped between the grasping pieces 15 and 16. In a state where the blood vessel is grasped, the detector 41 detects the parameter regarding the kind of blood vessel grasped between the grasping pieces 15 and 16 (e.g., the quantities of two kinds of light detected by the light receiving element 43 (see FIG. 3)). Further, for example, a high-frequency current is applied to the blood vessel as the treatment energy, and a sealing treatment of the grasped blood vessel is conducted. Note that the detection of the parameter by the detector 41 is performed before an operation to output electric energy from the energy output sources 32 and 47 or the like (an operation to apply the treatment energy to the grasped blood vessel) is input with the operational button 18.

Figure 4:
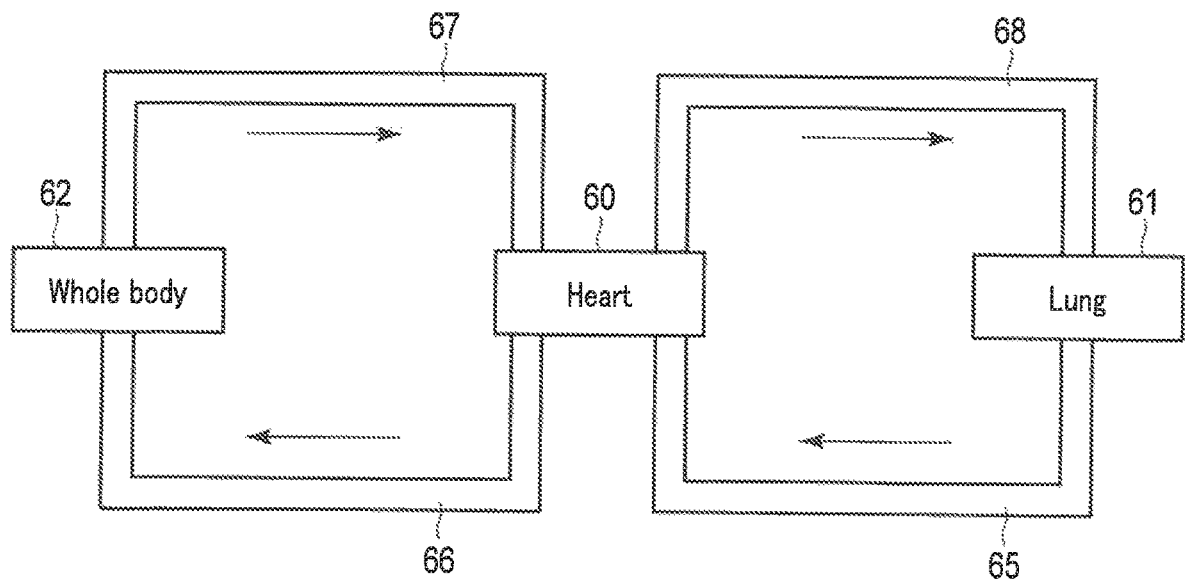
FIG. 4 is a schematic diagram showing the flow of blood in a human body.

FIG. 4 is a diagram showing the flow of blood in a human body. As shown in FIG. 4, a pulmonary circulation artery 68 and a pulmonary circulation vein 65 extend from a heart 60 to a lung 61, and a circulatory system artery 66 and a circulatory system vein 67 extend from the heart 60 to the whole body 62. A circulation path to guide blood from the heart 60 to the whole body 62 through the circulatory system artery 66 and return the blood to the heart 60 from the whole body 62 through the circulatory system vein 67 is referred to as a systemic circulation, and a blood vessel which forms the systemic circulation is referred to as a blood vessel of the circulatory system. Moreover, a circulation path to guide blood from the heart 60 to the lung 61 through the pulmonary circulation artery 68 and return the blood to the heart 60 from the lung 61 through the pulmonary circulation vein 65 is referred to as a pulmonary circulation, and a blood vessel which forms the a pulmonary circulation is referred to as a blood vessel of the pulmonary circulation. That is, the kinds of blood. vessels which are treated targets can be classified into two kinds of blood vessels of the circulatory system and the pulmonary circulation.

Oxygen is supplied to blood in the lung 61. Thus, blood relatively high in the oxygen concentration X guided to the whole body 62 from the lung 61 through the heart 60 flows to the pulmonary circulation vein 65 and the circulatory system artery 66, in the whole body 62, the oxygen in the blood is consumed. Thus, blood relatively low in the oxygen concentration X guided to lung 61 from the whole body 62 through the heart 60 flows to the circulatory system vein 67 and the pulmonary circulation artery 68. Accordingly, the oxygen concentration X in the pulmonary circulation artery 68 is lower than the oxygen concentration X in the circulatory system artery 66. That is, arteries are lower in the oxygen concentration X in the pulmonary circulation than in the circulatory system. Moreover, the oxygen concentration X in the pulmonary circulation vein 65 is higher than the oxygen concentration X in the circulatory system vein 67. That is, veins are higher in the oxygen concentration X in the pulmonary circulation than in the circulatory system.

Figure 5:
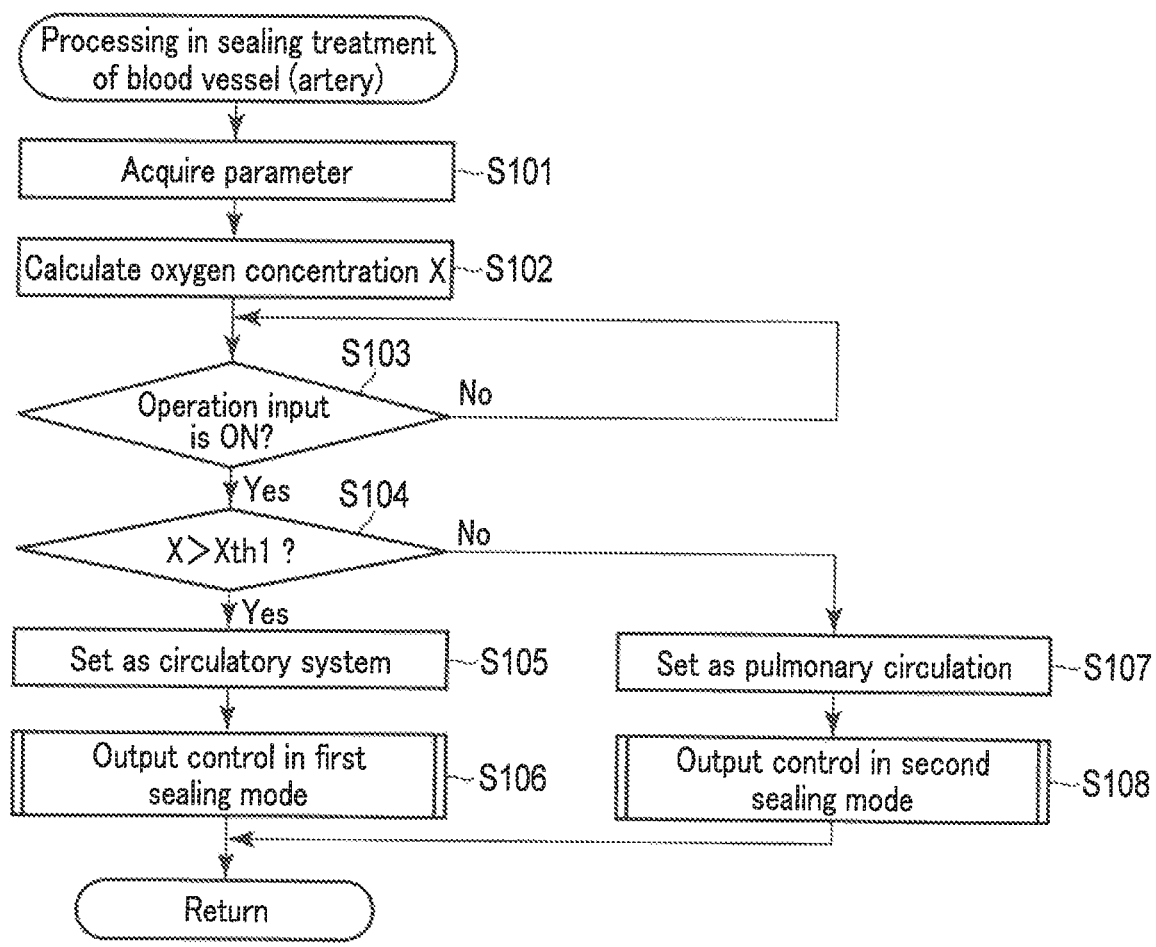
FIG. 5 is a flowchart showing processing at a processor in a sealing treatment of a blood vessel using the treatment system according to the first embodiment.

FIG. 5 is a flowchart showing processing at the processor 21 in a sealing treatment of a blood vessel (artery) using the treatment system 1 according to the first embodiment. As shown in FIG. 5, when the sealing treatment of the blood vessel (artery) is conducted, the processor 21 acquires the parameter regarding the kind grasped blood vessel (e.g., quantities of two kinds of light detected by the light receiving element 43) before the application of the treatment energy to the blood vessel) (step S101). That is, a state where the blood vessel is grasped between the grasping pieces 15 and 16, a detection result in the detector 41 is acquired. Then the processor 21 calculates the oxygen concentration X of the grasped blood vessel on the basis of the acquired detection result of the parameter (step S102). In this instance, for example, the ratio of the quantity of each of the two kinds of light detected by the light receiving element 43 to the total light quantity is calculated, and a table or the like indicating the relation between the calculated ratio and the oxygen concentration X of the grasped blood vessel is stored in the storage medium 22. Further, the oxygen concentration X is calculated by use of this table.

Furthermore, the processor 21 judges whether or not an operation input with the operational button (energy operation input section) 18 is performed (i.e., whether an operation input is on or off) (step S103). When the operation input is not performed (step S103—No), the processing returns to step S103, and waits until an operation input is performed with the operational button 18. When the operation input is performed (step S103—Yes), the setting section 25 of the processor 21 judges whether or not the calculated oxygen concentration X is higher than the oxygen concentration threshold Xth1 (step S104). That is, whether or not the oxygen concentration X is less than or equal to the oxygen concentration threshold Xth1 is judged. As described above, arteries are lower in the oxygen concentration X in the pulmonary circulation. than in the circulatory system. Thus, when the oxygen concentration X is higher than the oxygen concentration threshold Xth1 (step S104—Yes), the setting section 25 sets that the grasped blood vessel is a blood vessel of the circulatory system. (step S105). Further, the output controller 26 of the processor 21 performs output control of the electric energy from the energy output source 32 in a first sealing mode (step S106). When the oxygen concentration X is less than or equal to the oxygen concentration threshold Xth1 (step S104—No), the setting section 25 sets that the grasped blood vessel is a blood. vessel of the pulmonary circulation (step S107). Further, the output controller 26 performs output control of the electric energy from the energy output source 32 in a second sealing mode different from the first sealing mode (step S108).

Figure 6:
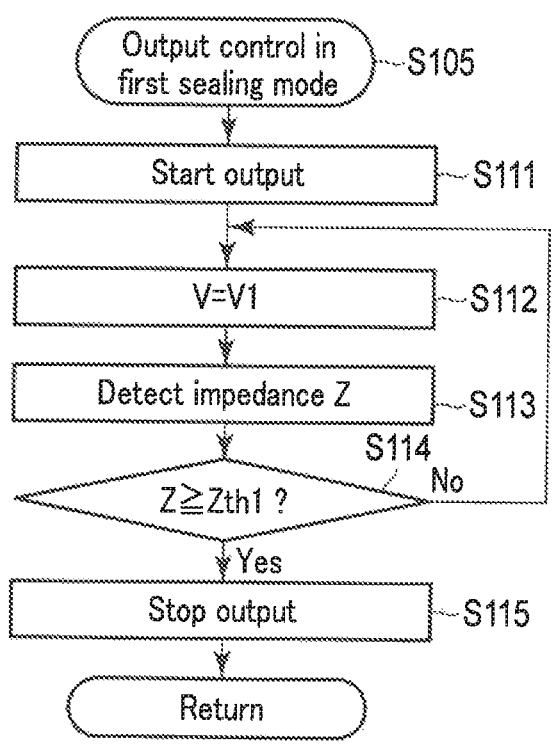
FIG. 6 is a flowchart showing processing in output control in a first sealing mode by the processor according to the first embodiment.

FIG. 6 is a flowchart showing processing by the processor 21 in the output control in the first sealing mode. As shown in FIG. 6, in the output control in the first sealing mode, the processor 21 starts the output of the electric energy (high-frequency electric power) from the energy output source (first energy output source) 32 (step S111). Accordingly, the electric energy is supplied to the electrodes 27 and 28, a high-frequency current flows to the grasped blood vessel, and the blood vessel is sealed.

When a given length of time elapses from the start of the output of the electric energy from the energy output source 32, the output controller 26 performs constant voltage control to maintain, with time, the output voltage from the energy output source 32 at a constant level of a first voltage value V1 (step S112). Moreover, when the output of the electric energy from the energy output source 32 is started, the impedance detector 23 of the processor 21 detects the impedance z between the grasping pieces 15 and 16 (i.e., impedance of the grasped treated target) on the basis of the detection result of the output current I in the current detection circuit 35 and the detection result of the output voltage V in the voltage detection circuit 36 (step S113). Then the processor 21 judges whether or not the detected impedance Z is equal to or more than an impedance threshold. (first impedance threshold) Zth1 (step S114). The impedance threshold Zth1 may be set by the surgeon or the like, or may be stored in the storage medium 22.

When the impedance Z is lower than the impedance threshold Zth1 (step S114—No), the processing returns to step S112, and the processing in and after step S112 is sequentially performed. When the impedance Z is equal to or more than the impedance threshold Zth1 (step S114—Yes), the output controller 26 stops the output of the electric energy high-frequency electric power) from the energy output source 32 (step S115). Thereby, the supply of the electric energy to the electrodes 27 and 28 is stopped. The processor 21 performs the output control of the electric energy from the energy output source 32 in the first sealing mode, and the energy treatment instrument 2 is thereby actuated in the first mode to coagulate the grasped treated target (blood vessel).

In the output control in the second sealing mode as well as in the output control in the first sealing mode, the processor 21 performs the processing in steps S111 and S113 to S115. However, in the second sealing mode, when a given length of time elapses from the start of the output of the electric energy from the energy output source 32, the output controller 26 performs constant voltage control to maintain, with time, the output voltage V from the energy output source 32 at a constant level of a second voltage value V2 lower than the first voltage value V1, Because the constant voltage control is performed at the second voltage value V2 lower than the first voltage value V1, the electric energy output from the energy output source 32 is lower in the second sealing mode than in the first sealing mode. That is, the output controller 26 of the processor 21 makes the electric energy output from the energy output source 32 lower in the second sealing mode than in the first sealing mode. The processor 21 performs the output control of the electric energy from the energy output source 32 in the second sealing mode, and the energy treatment instrument 2 thereby coagulates the grasped treated target. (blood vessel) and is actuated in the second mode different from the first mode. As described above, in the present embodiment, the processor 21 switches the actuation state of the energy treatment instrument 2 between the first mode (first actuation mode) and the second mode (second actuation mode) by controlling the output of the electric energy from the energy output source on the basis of the setting of the kind of grasped blood vessel. The output state of the electric energy from the energy output source 32 varies between the first sealing mode and the second sealing mode, so that in the energy treatment instrument 2, the state of the application of the treatment energy (high-frequency current) to the grasped treated target (blood vessel) from the energy application section (the grasping pieces 15 and 16) varies between the first mode and the second mode.

Note that if the electric energy output from the energy output source 32 is lower in the second sealing mode than in the first sealing mode, the output control may be performed in a way other than the constant voltage control in each of the first and second sealing modes. For example, in a certain example, in the first sealing mode, the output controller 26 performs constant electric power control to maintain, with time, the output electric power P from the energy output source 32 at a constant level of first electric power 21. Further, in the second sealing mode, the output controller 26 performs constant electric power control to maintain, with time, the output electric power P from the energy output source 32 at a constant level of second electric power P2 lower than the first electric power P1. In another certain example, in the first sealing mode, it is possible to perform both the constant voltage control to maintain, with time, the output voltage V at a constant level of the first voltage value V1 and the constant electric bower control to maintain, with time, the output electric power P at a constant level of the first electric power P1, and the switch is made between the constant voltage control and the constant electric power control in accordance with the impedance Z. Moreover, in the second sealing mode, it is possible to perform both the constant voltage control to maintain, with time, the output voltage V at a constant level of the second voltage value V2 lower than the first voltage value V1 and the constant electro bower control to maintain, with time, the output electric power P at a constant level of the second electric power P2 lower than the first electric power P1, and the switch is made between the constant voltage control and the constant electric power control in accordance with the impedance Z.

However, in each of the examples, the electric energy output from the energy output source 32 is lower in the second sealing mode than in the first sealing mode.

Furthermore, in the present embodiment, in each of the first and second sealing modes, the high-frequency current alone is applied to the blood vessel as the treatment energy, and treatment energy other than the high-frequency current, such as the ultrasonic vibration and the heater heat or the like, is not applied to the blood vessel (treated target). For example, in the example in which the ultrasonic transducer 46 is provided in the energy treatment instrument 2, the processor 21 stops the output of the electric energy to the ultrasonic transducer 46 from the energy output source 47 in each of the first and second sealing modes. Thus, in each of the first and second. sealing modes, the electric energy is not supplied to the ultrasonic transducer 46, and no ultrasonic vibration is generated in the ultrasonic transducer 46. Similarly, in the example in which the heater is provided in the energy treatment instrument 2, the processor 21 stops the output of the electric energy to the heater from the energy output source in each of the first and second sealing modes. Thus, in each of the first and second sealing modes, the electric energy is not supplied to the heater, and no heat is generated in the heater.

In a certain example, is the output control in the first sealing mode and the output control in the second sealing mode are finished, no electric energy is supplied to the electrodes 27 and 28, the ultrasonic transducer 46, and the heater or the like, and treatment energy such as the high-frequency current, the ultrasonic vibration, and the heater heat or the like is not applied to the treated target. In another certain example, if the output control in the first sealing mode and the output control in the second sealing mode are finished, a shift is automatically made to output control for a cutting mode. In this case, in the example in which the ultrasonic transducer 46 is provided in the energy treatment instrument 2, the processor 21 causes the electric energy to be output to the ultrasonic transducer 46 from the energy output source 47 at a cutting level (high output level), in the cutting mode. Accordingly, ultrasonic vibration is generated in the ultrasonic transducer 46, and the ultrasonic vibration is transmitted to one of the grasping pieces 15 and 16. Then the transmitted ultrasonic vibration is applied to the grasped blood vessel (treated target) as the treatment energy, and the blood vessel is cut open by frictional heat resulting from the ultrasonic vibration. Similarly, in the example in which the heater is provided in the energy treatment instrument 2, the processor 21 causes the electric energy to be output to the heater from the energy output source at the cutting level (high output level), in the cutting mode. Accordingly, heat is generated in the heater. Then the heater heat is applied to the grasped blood vessel as the treatment energy, and the blood vessel is cut open.

Figure 7:
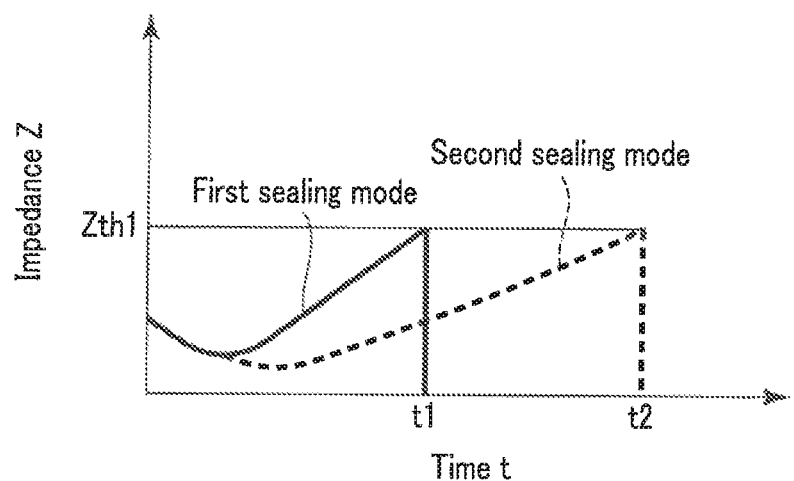
FIG. 7 is a schematic diagram showing one example of a change with time of impedance between a pair of grasping pieces in a state where the processor accords ng to the first embodiment is performing output control in each of the first and second sealing modes.

FIG. 7 is a diagram showing one example of a change with time of the impedance $Z$ between the pair of grasping pieces 15 and 16 (i.e., impedance of the grasped treated target) in a state where the processor 21 is performing output control in each of the first and second sealing modes. In FIG. 7, the impedance 7, is indicated on the vertical axis, and the time t based on the start of the output of the electric energy from the energy output source 32 is indicated on the horizontal axis. In FIG. 7, the change with time of the impedance 2 in the first sealing mode is indicated by a solid line, and the change with time of the impedance $Z$ in the second sealing mode is indicated by a broken line. As shown in FIG. 7, when the output of the electric energy from the energy output source 32 is started and the high-frequency current starts flowing through the blood vessel (treated target), the impedance normally shows a behavior of decreasing with time for a while. Further, when the impedance $Z$ decreases to some degree with time, the impedance $Z$ normally shows a behavior of increasing with time in response to the increase of the temperature of the treated target due to the heat resulting from the high-frequency current.

In the present embodiment, as described above, the electric energy output from the energy output source 32 is lower in the second sealing mode than in the first sealing mode. Thus, a calorific value per unit time generated due to the high-frequency current flowing through the blood vessel. (treated target) is lower in the second sealing mode than in the first sealing mode. Therefore, the increase rate of the temperature of the treated target (blood vessel) is lower, and the increase rate of the impedance $Z$ in a state where the impedance $Z$ increases with time is lower, in the second sealing mode than in the first sealing mode. Thus, the time for the impedance $Z$ to reach the impedance threshold $Zth1$ from the start of the output of the electric energy from the energy output source 32 is longer in the second sealing mode than in the first sealing mode. Actually, in one example in FIG. 7, the impedance $Z$ reaches the impedance threshold $Zth1$ at a time $t1$ in the first sealing mode, whereas the impedance $Z$ reaches the impedance threshold $Zth1$ at a time $t2$ after the time $t1$ in the second sealing mode. In the present embodiment, as described above, in each of the first and second sealing modes, the output of the electric energy from the energy output source 32 is stopped on the basis of the fact that the impedance $Z$ is equal to or more than the impedance threshold $Zth1$. Therefore, the output time of the electric energy from the energy output source 32 is longer in the second sealing mode than in the first sealing mode.

As described above, the output controller 26 (the processor 21) makes the electric energy output from the energy output source 32 lower and makes the output time of the electric energy from the energy output source 32 longer in the second sealing mode than in the first sealing mode. Thus, the calorific value per unit time generated due to the high-frequency current in the blood vessel is lower, and the time of the application of the high-frequency current to the blood vessel is longer in the second sealing mode than in the first sealing mode. That is, in the energy treatment instrument 2, the time of the application of the treatment energy (high-frequency current) to the treated target (blood vessel) from the energy application section (the grasping pieces 15 and 16) is longer in the second mode (second actuation mode) than in the first mode (first actuation mode). The magnitude of the total quantity of the treatment energy (high frequency current) applied to the treated target in the first sealing mode corresponds to, for example, the magnitude of the area between the impedance $Z$ and the time t indicated by the solid line in FIG. 7. Moreover, the magnitude of the total quantity of the treatment energy (high-frequency current) applied to the treated target in the second sealing mode corresponds to, for example, the magnitude of the area between the impedance $Z$ and the time t indicated by the broken line in FIG. 7. Here, in FIG. 7, the area under the impedance a in the second sealing mode indicated by the broken line is larger than the area under the impedance $Z$ in the first sealing mode indicated by the solid line. Therefore, the performance of sealing the blood vessel by the high-frequency current is higher in the second sealing mode than in the first sealing mode.

The blood vessel of the circulatory system and the blood vessel oil the pulmonary circulation are different from each other in wall thickness. Thus, there is concern that the treatment of sealing the grasped blood vessel. using treatment energy such as the high-frequency current may be affected if the blood vessel of the pulmonary circulation is sealed as the treated target as in the case where the blood vessel of the circulatory system is sealed. Accordingly, there is a possibility that performance of sealing the blood vessel, such as a pressure resistance value of the sealed blood vessel, may be affected, in the present embodiment, the detector 41 detects the quantity of each of the two kinds of light received by the light receiving element 43, and the processor 21 calculates the oxygen concentration X on the basis of the detection result in the detector 41. When the oxygen concentration X is higher than the oxygen concentration threshold Xth1, it is set that the grasped blood vessel is a blood vessel of the circulatory system, and the output control is performed in the first sealing mode. When the oxygen concentration X is less than or equal to the oxygen concentration threshold Xth1, it is set that the grasped blood vessel is a blood vessel of the pulmonary circulation, and the output control is performed in the second sealing mode. Thus, the electric energy output from the energy output source 32 is lower and the output time of the electric energy from the energy output source 32 is longer when it is set that the grasped blood vessel is a blood vessel of the pulmonary circulation than when it is set that the grasped blood vessel is a blood vessel of the circulatory system. That is, in the energy treatment instrument 2, the time of the application of the treatment energy (high-frequency current) to the treated target (blood vessel) from the energy application section (the grasping pieces 15 and 16) is longer in the second mode (second actuation mode) in the case where it is set that the grasped blood vessel is a blood vessel of the pulmonary circulation than in the first mode (first actuation mode) in the case where it is set that the grasped blood vessel is a blood vessel of the circulatory system. Therefore, the case where the grasped blood vessel is a blood vessel of the pulmonary circulation, in contrast to the case where the grasped blood vessel is a blood vessel of the circulatory system, the treatment is conducted in the second sealing mode in which the performance of sealing the blood vessel by the high-frequency current of the energy treatment instrument 2 of the treatment system 1 is higher than that in the first sealing mode, so that the blood vessel is sealed at the same level as in the case where the grasped blood vessel a blood vessel of the circulatory system. Consequently, by the use of the energy treatment instrument 2 of the treatment system 1, performance of sealing the blood vessel, such as a pressure resistance value (difficulty of the flow of blood to the sealed portion) of the sealed blood vessel, is easily maintained when the grasped blood vessel is a blood vessel of the pulmonary circulation as well.

As described above, in the present embodiment, even when the treated target (blood vessel) is a blood vessel of the pulmonary circulation, the grasped blood vessel is properly sealed by the increase of the performance of sealing the blood vessel using the high-frequency current. That is, in accordance with the kind of blood vessel, the blood vessel is properly sealed by use of treatment energy such as the high-frequency current, and suitable treatment performance (sealing performance) is achieved. Therefore, suitable treatment performance is achieved regardless of the kind of blood vessel.

Modification of First Embodiment

Note that in a first modification of the first embodiment, processing by the processor 21 in the output control in the second sealing mode is different from that in the first embodiment. In the present modification as well, the processor 21 performs processing similar to that in the first embodiment in the output control in the first sealing mode (see FIG. 6). In the output control in the second sealing mode as well as in the output control in the first sealing mode, the processor 21 performs processing in steps S111 to S113. However, in the second sealing mode, instead of the processing in step S114, the processor 21 judges whether or not the detected impedance Z is equal to or more than an impedance threshold (second impedance threshold) Zth2. Here, the impedance threshold Zth2 is higher than the impedance threshold (first impedance threshold) Zth1. Moreover the impedance threshold Zth2 may be set by the surgeon or the like, or may be stored in the storage medium 22.

Furthermore, when the impedance Z is lower than the impedance threshold Zth2, the processing returns to step S112, and the processing in and after step S112 is sequentially performed. When the impedance Z is equal to or more than the impedance threshold Zth2, the output controller 26 stops the output of the electric energy (high-frequency electric power) from the energy output source 32. Therefore, in the second sealing mode according to the present modification, the output of the electric energy from the energy output source 32 is stopped on the basis of the fact that the impedance Z is equal to or more than the impedance threshold second impedance threshold.) Zth2 higher than the impedance threshold (first impedance threshold) Zth1. In the present modification as well, the processor 21 switches the actuation state of the energy treatment instrument 2 between the first mode (first actuation mode) and the second mode (second actuation mode) by controlling the output of the electric energy from the energy output source 32 on the basis of the setting of the kind of grasped blood vessel. Moreover, in the present modification as well, the output state of the electric energy from the energy output source 32 varies between the first sealing mode and the second sealing mode, so that in the energy treatment instrument 2, the state of the application of the treatment energy (high-frequency current) to the grasped treated target (blood vessel) from the energy application section (the grasping pieces 15 and 15) varies between the first mode and the second mode.

Figure 8:
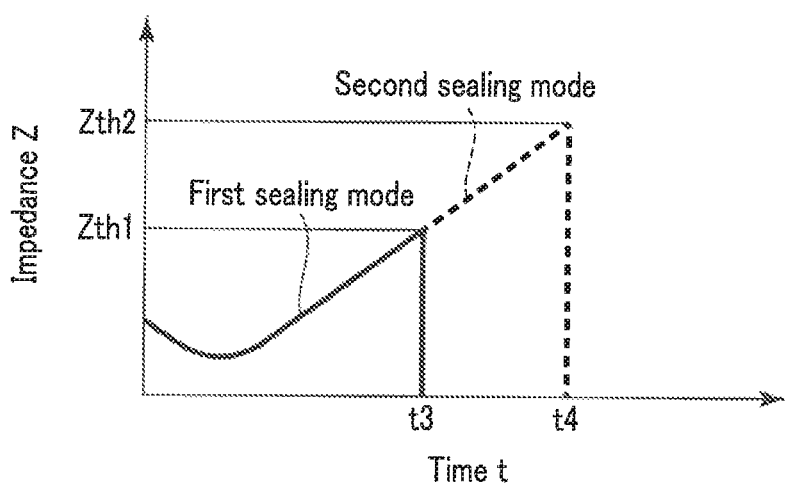
FIG. 8 is a schematic diagram showing one example of a change with time of the impedance between the pair of grasping pieces in a state where the processor according to a first modification of the first embodiment is performing output control in each of the first and second sealing modes.

FIG. 8 is a diagram showing one example of a change with time of the impedance Z between the pair of grasping pieces 15 and 16 in a state where the processor 21 according to the present modification is performing output control in each of the first and second sealing modes. In FIG. 8, the impedance Z is indicated on the vertical axis, and the time t based on the start of the output of the electric energy from the energy output source 32 is indicated on the horizontal axis. In FIG. 8, the change with time of the impedance Z in the first sealing mode is indicated by a solid line, and the change with time of the impedance Z in the second sealing mode is indicated by a broken line.

As described above, in the present modification, the output of the electric energy from the energy output source 32 is stopped on the basis of the fact that the impedance Z is equal to or more than the impedance threshold Zth1 in the first sealing mode, whereas the output of the electric energy from the energy output source 32 is stopped on the basis of the fact that the impedance Z is equal to or more than the impedance threshold Zth2 in the second sealing mode. Moreover, the impedance threshold Zth2 is higher than the impedance threshold Zth1. Thus, the output time of the electric energy from the energy output source 32 is longer in the second sealing mode than in the first sealing mode.

Actually, in one example in FIG. 8, the output of the electric energy is stopped at a time t3 in the first sealing mode, whereas the output of the electric energy is stopped at a time t4 after the time t3 in the second sealing mode.

As described above, in the present modification, the output controller 26 (the processor 21) sets a higher impedance threshold (Zth1; Zth2) to be the reference to stop the output in the second sealing mode than in the first sealing mode so that the output time of the electric energy from the energy output source 32 is longer in the second sealing mode than in the first sealing mode. That is, in the energy treatment instrument 2 according to the present modification as well, the time of the application. of the treatment energy (high-frequency current) to the treated target (blood vessel) from the energy application section (the grasping pieces 15 and 16) is longer in the second mode (second actuation mode) in the case where it is set that the grasped blood vessel is a blood vessel of the pulmonary circulation than in the first mode (first actuation mode) in the case where it is set that the grasped blood vessel is a blood vessel of the circulatory system. Thus, the time of the application of the high-frequency current to the blood vessel is longer, and the total quantity of the treatment energy (high-frequency current) applied to the blood vessel is greater, so that the performance of sealing the blood vessel by the high-frequency current is higher in the second sealing mode than in the first sealing mode. Therefore, in the present modification as well, when the grasped blood vessel is a blood vessel of the pulmonary circulation, the treatment is conducted in the second sealing mode in which the performance of sealing the blood vessel by the high-frequency current of the energy treatment instrument 2 of the treatment system 1 is higher than that in the first sealing mode, so that the blood vessel is sealed at the same level as in the case where the grasped blood vessel is a blood vessel of the circulatory system. Consequently, by the use of the energy treatment instrument 2 of the treatment system 1, performance of sealing the blood vessel, such as a pressure resistance value (difficulty of the flow of blood to the sealed portion) of the sealed blood vessel, is easily maintained when the grasped blood vessel is a blood vessel of the pulmonary circulation.

Note that in a certain modification, the first embodiment may be combined with its first modification. In this case, the processor 21 makes the electric energy output from the energy output source 32 lower and sets a higher impedance threshold (Zth1; Zth2) to be the reference to stop the output in the second sealing mode than in the first sealing mode. In the present modification as well, the output state of the electric energy from the energy output source 32 varies between the first sealing mode and the second sealing mode, so that in the energy treatment instrument 2, the state of the application of the treatment energy (high-frequency current) to the grasped treated target (blood vessel) from the energy application section (the grasping pieces 15 and 16) varies between the first mode and the second mode.

Figure 9:
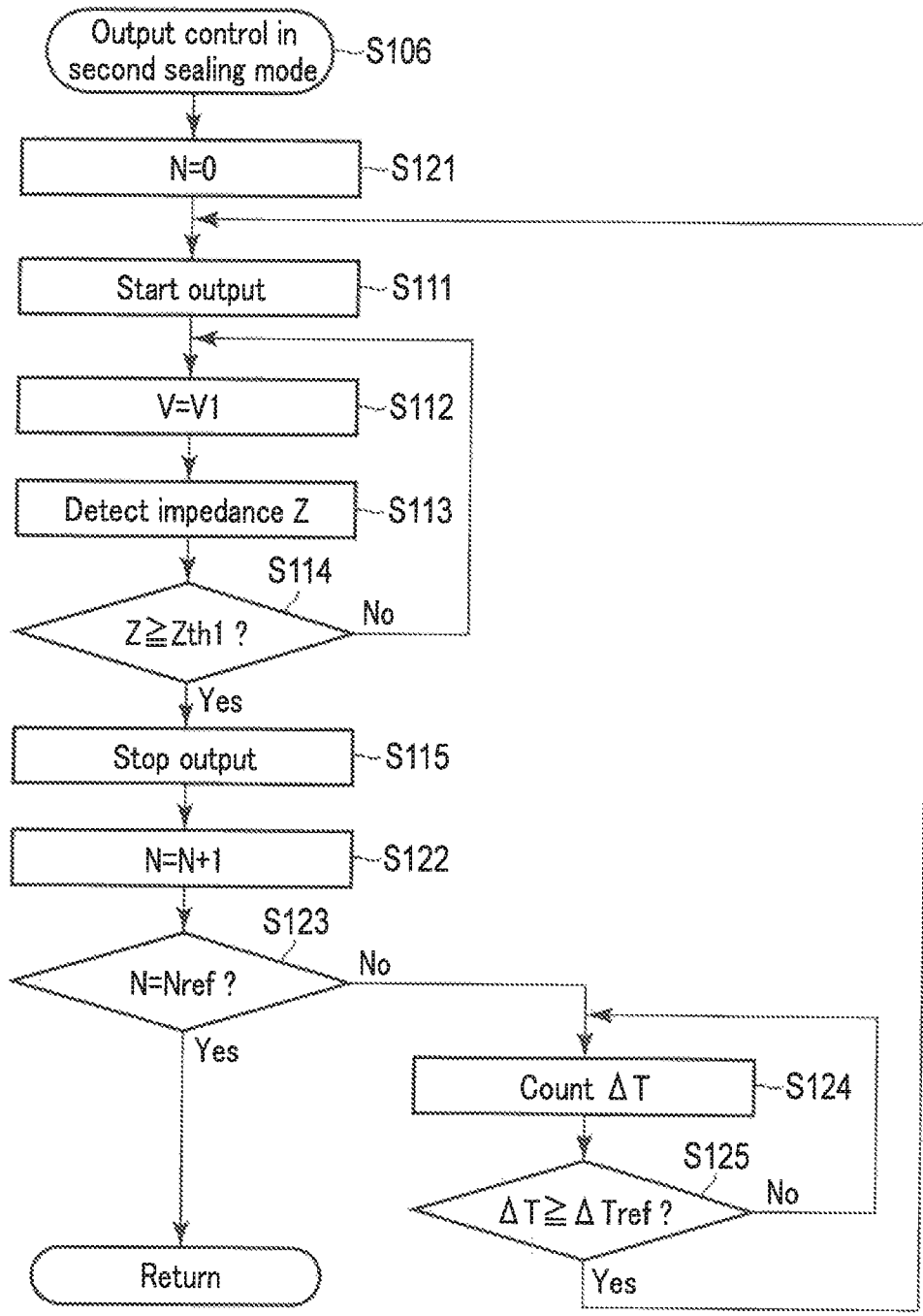
FIG. 9 is a flowchart showing processing in output control in the second sealing mode by the processor according to a second modification of the first embodiment.

Furthermore, in the second modification of the first embodiment, the processor 21 performs processing shown in FIG. 9 in the output control in the second sealing mode. In the present modification as well, the processor 21 performs processing similar to that in the first embodiment in the output control in the first sealing mode (see FIG. 6). In the present modification, in the output control in the second sealing mode, the number of outputs N of the electric energy from the energy output source 32 is defined as a parameter. In the output control in the second sealing mode, the processor 21 sets the number of outputs N at 0 as an initial value (step S121). Further, as in the output control in the first sealing mode, the processor 21 performs the processing in steps S111 to S115.

If the output of the electric energy from the energy output source 32 is stopped by the processing in step S115, the processor 21 adds one to the number of outputs N (step S122). Then the processor 21 judges whether or not the number of outputs N after the addition is the same as a reference number of times Nref (step S123). The reference number of times Nref is a natural number of 2 or more, and may be set by the surgeon or the like, or may be stored in the storage medium 22. When the number of outputs N is the same as the reference number of times Nref, that is, when the number of outputs N has reached the reference number of times Nref (step S123—Yes), the processor 21 finishes the output control in the second sealing mode. Consequently, for example, the output of the electric energy from the energy output source 32 is continuously kept stopped, Here, a time (elapsed time) ΔT at which a point nearest the point where the output of the electric energy from the energy output source 32 is stopped by the processing in step S115 is 0 is defined. When the number of outputs N is not the same as the reference number of times Nref, that is, when the number of outputs N has not reached the reference number of times Nref (step S123—No), the processor 21 counts the time ΔT (step S124). Then the processor 21 judges whether or not the time ΔT that is being counted is equal to or more than a reference time ΔTref (step S125). The reference time ΔTref is, for example, 10 msec, and may be set by the surgeon or the like, or may be stored in the storage medium 22.

When the time ΔT is shorter than the reference time ΔTref (step S125—No), the processing returns to step S124, and the processing in and after step S124 is sequentially performed. That is, the output of the electric energy from the energy output source 32 is kept stopped, and the time ΔT is continuously counted. When the time ΔT is equal to or more than the reference time ΔTref (step S125—Yes), the processing returns to step S111, and the processing in and after step S111 is sequentially performed. That is, the electric energy is again output from the energy output source 32.

The processing described above is performed, so that in the output control in the second sealing mode, the output controller 26 of the processor 21 stops the output of the electric energy from the energy output source 32 after starting the output of the electric energy from the energy output source 32, and again starts the output of the electric energy from the energy output source 32 after once stopping the output of the electric energy from the energy output source 32. That is, in the second sealing mode, the electric energy is again output from the energy output source 32 when the reference time ΔTref elapses from the point where the output of the electric energy from the energy output source 32 is once stopped. Moreover, in the output control in the second sealing mode, the processor 21 causes the electric energy to be intermittently output from the energy output source 32 the reference number of times Nref (more than one time). In the present modification as well, the processor 21 switches the actuation state of the energy treatment instrument 2 between the first mode (first actuation mode) and the second mode (second actuation mode) by controlling the output of the electric energy from the energy output source 32 on the basis of the setting of the kind of grasped blood vessel. In the present modification as well, the output state of the electric energy from the energy output source 32 varies between the first sealing mode and the second sealing mode, so that in the energy treatment instrument 2, the state of the application of the treatment energy (high, frequency current) to the grasped treated target (blood vessel) from the energy application section (the grasping pieces 15 and 16) varies between the first mode and the second mode.

Figure 10:
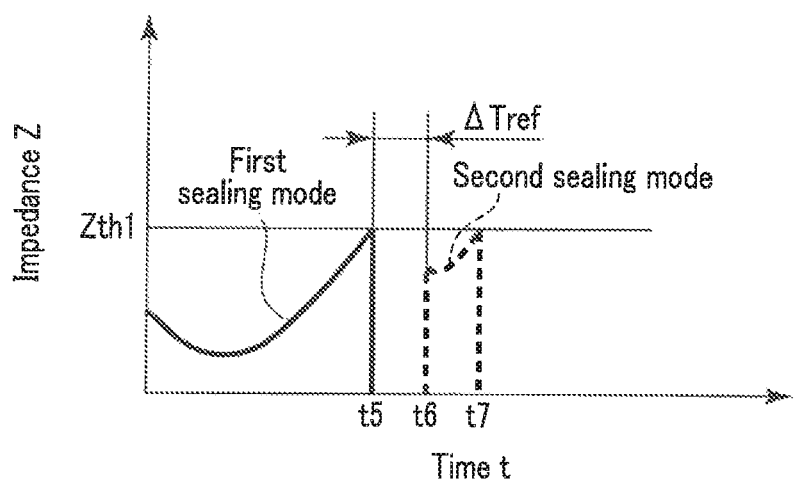
FIG. 10 is a schematic diagram showing one example of a chancre with time of the impedance between the pair of grasping pieces in a state where the processor according to the second modification of the first embodiment is performing output control in each of the first and second sealing modes.

FIG. 10 is a diagram showing one example of a change with time of the impedance Z between the pair of grasping pieces 15 and 16 in a state where the processor 21 according to the present modification is performing output control in each of the first and second sealing modes. In FIG. 10, the impedance Z is indicated on the vertical axis, and the time t based on the start of the output of the electric energy from the energy output source 32 is indicated on the horizontal axis in FIG. 10, the chance with time of the impedance Z in the first sealing mode is indicated by a solid line, and the change with time of the impedance Z in the second sealing mode is indicated by a broken line. In one example shown in FIG. 10, in each of the first and second sealing modes, the output of the electric energy from the energy output source 32 is stopped at a time t5 on the basis of the fact that the impedance Z has reached the impedance threshold Zth1.

As described above, in the present modification, the electric energy is intermittently output from the energy output source 32 more than one time (the reference number of times Nref) in the second sealing mode. Thus, in one example shown in FIG. 10, in the second sealing mode, the output of the electric energy from the energy output source 32 is again started at a time t6 at which the reference time ΔTref elapses from the time t5 when the output is stopped. In this instance, the impedance Z is lower than the impedance threshold Zth1. Further, at a time t7 after the time t6 (the time at which the output of the electric energy is again started), the output of the electric energy from the energy output source 32 is again stopped on the basis of the fact that the impedance Z has reached the impedance threshold Zth1. Note that the reference number of times Nref is 2 the example in FIG. 10.

As described above, in the present modification, the output controller 26 (the processor 21) again starts the output of the electric energy after once stopping the output, in the second sealing mode. Thus, the output time of the electric energy from the energy output source 32 is longer, and the time of the application of the high-frequency current to the blood vessel is longer in the second sealing mode than in the first sealing mode. That is, in the energy treatment instrument 2 according to the present modification as well, the time of the application of the treatment energy (high-frequency current) to the treated target (blood vessel) from the energy application section (the grasping pieces 15 and 16) is longer in the second mode (second actuation mode) in the case where it is set that the grasped blood vessel is a blood vessel of the pulmonary circulation than in the first mode (first actuation mode) in the case where it is set that the grasped blood vessel is a blood vessel of the circulatory system. Thus, the performance of sealing the blood vessel by the high-frequency current is higher in the second sealing mode than in the first sealing mode. Therefore, in the present modification as well, when the grasped blood vessel is a blood vessel of the pulmonary circulation, the treatment is conducted in the second sealing mode in which the performance of sealing the blood vessel by the high-frequency current of the energy treatment instrument 2 of the treatment system 1 is higher than that in the first sealing mode, so that the blood vessel is sealed at the same level as in the case where the grasped blood vessel is a blood vessel of the circulatory system. Consequently, by the use of the energy treatment instrument 2 of the treatment system 1, perfor-mance of sealing the blood vessel, such as a pressure resistance value (difficulty of the flow of blood to the sealed portion) of the sealed blood vessel, is easily maintained when the grasped blood. vessel is a blood vessel of the pulmonary circulation as well.

Figure 11:
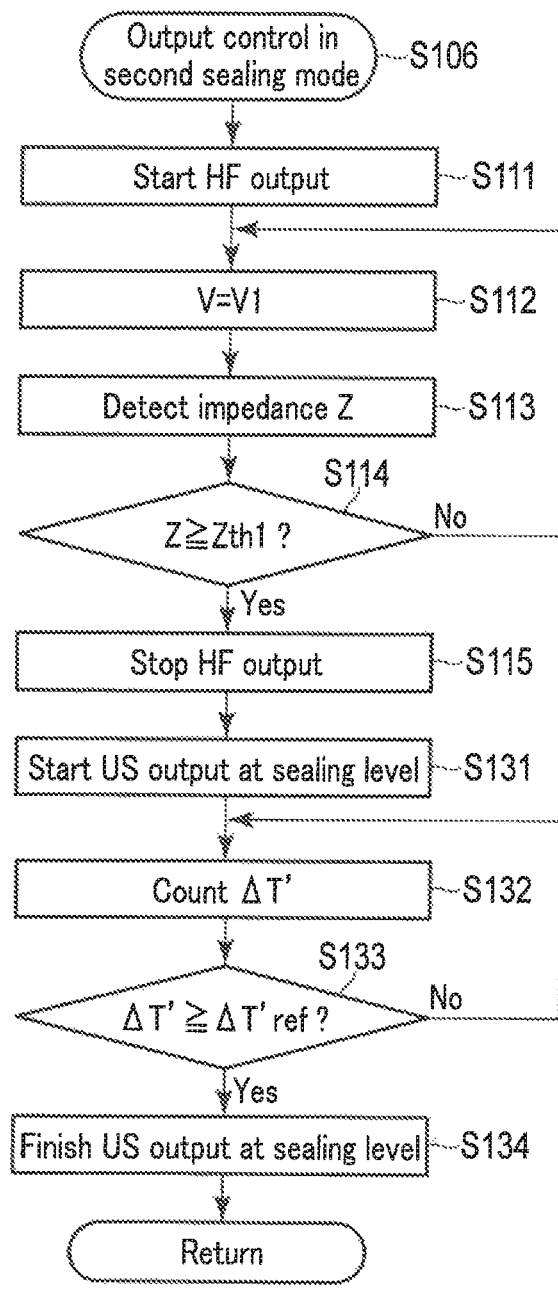
FIG. 11 is a flowchart showing processing in output control in the second sealing mode by the processor according to a third modification of the first embodiment.

Furthermore, in a third modification of the first embodiment, the processor 21 performs the processing shown in FIG. 11 in the output control in the second sealing mode. In the present modification as well, the processor 21 performs processing similar to that in the first embodiment in the output control in the first sealing mode (see FIG. 6). Further, in the output control in the second sealing mode as well as in the output control in the first sealing mode, the processor 21 performs the processing in steps S111 to S115.

In the second sealing mode, when the output of the electric energy from the energy output source 32 is stopped by the processing in step S115, the output controller 26 of the processor 21 starts the output of the electric energy to the ultrasonic transducer 46 from the energy output source 47 (step S131). In this instance, the electric energy is output at a sealing level of a low output level in the energy output source 47. That is, the output level is lower in the output of the electric energy at the sealing level than in the output of the electric energy at the cutting level described above. Thus, the electric energy supplied to the ultrasonic transducer 46 is lower, and the amplitude of the ultrasonic vibration transmitted to one of the grasping pieces 15 and 16 is lower in the output at the sealing level than in the output at the cutting level Therefore, in the output at the sealing level, the calorific value of the frictional heat resulting from the ultrasonic vibration is low, the grasped blood. vessel is not cut open by the frictional heat, and the blood vessel is only sealed. Note that in FIG. 13, the output of the electric energy to the electrodes 27 and 28 from the energy output source 32 is indicated as high-frequency (HF) output, and the output of the electric energy to the ultrasonic transducer 46 from the energy output source 47 is indicated as ultrasonic (US) output.

Here, a time (elapsed time) ΔT' at which a point where the output of the electric energy from the energy output source 47 at the sealing level is started by the processing in step S131 (a point where the output from the energy output source 32 is stopped by the processing in step S115) is 0 is defined. When the output of the electric energy from the energy output source 47 at the sealing level is started, the processor 21 counts the time ΔT' (step S132). Then the processor 21 judges whether or not the time ΔT' that is being counted is equal to or more than a reference time ΔT' ref (step S133) The reference time ΔT' ref may be set by the surgeon or the like, or may be stored in the storage medium 22.

When the time ΔT' is shorter than the reference time ΔT' ref (step S133—No), the processing returns to step S132, and the processing in and after step S132 is sequentially performed. That is, the time ΔT' continuously counted. When the time ΔT' is equal to or more than the reference time ΔT'ref (step S133—Yes), the output controller 26 finishes the output of the electric energy from the energy output source 47 at the sealing level (step S134). In this instance, the output of the electric energy to the ultrasonic transducer 46 from the energy output source 47 may be stopped, a shift may be automatically made to The output control in the cutting mode, and a switch may be automatically made so that the electric energy is output to the ultrasonic transducer 46 at the cutting level (high output level). Moreover, in a certain example, the output controller 26 may finish the output of the electric energy from the energy output source 47 at the sealing level on the basis of the fact that the operation input with the operational button (energy operation input section) 18 is cancelled. (i.e., the fact that the operation input is turned off), instead of steps S132 and S133.

As described above, in the present modification, the output controller 26 (the processor 21) starts The output of the electric energy to the ultrasonic transducer 46 after stopping the output of the electric energy to the electrodes 27 and 28, in the second sealing mode. That is, the processor 21 switches the actuation state of the energy treatment instrument 2 between the first mode (first actuation mode) and the second mode (second actuation mode) by controlling the output of the electric energy from the energy output sources 32 and 47 on the basis of the setting of the kind of grasped blood vessel. Moreover, in the present modification, the electric energy is output from the energy output source 47 in the second sealing mode alone, so that in the energy treatment instrument 2, the state of the application of the treatment energy (high-frequency current and ultrasonic vibration) to the grasped treated target (blood vessel) from the energy application section (the grasping pieces 15 and 16) varies between the first mode and the second mode. Thus, in the second sealing mode, the grasped blood vessel is sealed by the ultrasonic vibration (frictional heat) even after the output of the electric energy to the electrodes 27 and 28 is stopped. That is, in the second sealing mode, the impedance Z is higher, so that the blood vessel is sealed by the frictional heat resulting from the ultrasonic vibration even in a state where it is difficult for the high-frequency current to flow through the blood vessel. Thus, the performance of sealing the blood vessel by the treatment energy is higher in the second sealing mode than in the first sealing mode. Therefore, in the present modification as well, when the grasped blood vessel is a blood vessel of the pulmonary circulation, the treatment is conducted in the second sealing mode in which the performance of sealing the blood vessel by the high-frequency current of the energy treatment instrument 2 of the treatment system 1 is higher than that in the first sealing mode, so that the blood vessel is sealed at the same level as in the case where the grasped blood vessel is a blood vessel of the circulatory system. Consequently, by the use of the energy treatment instrument 2 of the treatment system 1, performance of sealing the blood vessel, such as a pressure resistance value (difficulty of the flow of blood to the sealed portion) of the sealed blood vessel, is easily maintained when the grasped blood vessel is a blood vessel of the pulmonary circulation as well.

Note that in a certain modification, in the second sealing mode, when the output of the electric energy from the energy output source 32 is stopped by the processing in. step S115, the output controller 26 of the processor 21 starts the output of the electric energy to the heater. In this instance as well, the electric energy is output at the sealing level which is lower in the output level than the cutting level, described above. Thus, the electric energy supplied to the heater is lower in the output at the sealing level than in the output at the cutting level. Therefore, in the output at the sealing level, the calorific value of the heat generated in the heater is lower, the grasped blood vessel is not cut open by the heater heat, and the blood vessel is only sealed. In the present modification, the blood vessel is sealed by the heater heat in addition to the high-frequency current in the second sealing mode. That is, in the present modification as well, in the energy treatment instrument 2, the state of the application of the treatment energy (high-frequency current and heater heat) to the grasped treated target (blood vessel) from the energy application section (the grasping pieces 15 and 16) varies between the first mode and the second mode. Therefore, the performance of sealing the blood vessel by the treatment energy is higher in the second sealing mode than in the first sealing mode. Thus, functions and advantageous effects similar to those in the third modification of the first embodiment are provided.

Furthermore, the output control of the electric energy in which the performance of sealing the blood vessel by the treatment energy is higher when it is set that the grasped blood vessel is a blood vessel of the pulmonary circulation than when it is set that the grasped blood vessel is a blood vessel of the circulatory system is also applicable to an example in which no high-frequency current is applied to the blood vessel and in which the treatment energy (ultrasonic vibration and heater heat or the like) other than the high-frequency current is only applied to the blood vessel. For example, in a certain modification in which the electric energy is output to the ultrasonic transducer 46 at the sealing level and the blood vessel is sealed by use of the ultrasonic vibration alone, the processor 21 makes the electric energy output to the ultrasonic transducer 46 from the energy output source 47 lower and makes the output time of the electric energy to the ultrasonic transducer 46 longer in the second sealing mode than the first sealing mode. Thus, the time of the application of the ultrasonic vibration to the blood vessel is longer, and the performance of sealing the blood vessel by the ultrasonic vibration is higher in the second sealing mode (the second mode of the energy treatment instrument 2 than in the first sealing mode (the first mode of the it energy treatment instrument 2). Moreover, in a certain modification in which the electric energy is output to the heater at the sealing level and the blood vessel is sealed. by the heater heat alone, the processor 21 makes the electric energy output to the heater from the energy output source lower and makes the output time of the electric energy to the heater longer in the second sealing mode than in the first sealing mode. Thus, the time of the application of the heater heat to the blood vessel is longer, and the performance of sealing the blood vessel by the heater heat is higher in the second sealing mode (when it is set that the grasped blood vessel is a blood vessel of the pulmonary circulation) than in the first sealing mode (when it is set that the grasped blood vessel is a blood vessel of the circulatory system). Consequently, by the use o the energy treatment instrument 2 of the treatment system 1, performance of sealing the blood vessel, such as a pressure resistance value (difficulty of the flow of blood to the sealed portion) of the sealed blood vessel, is easily maintained when the grasped blood vessel is a blood vessel of the pulmonary circulation as well.

Furthermore, in a certain modification, the surgeon or the like may judge whether to cause the processor 21 to perform the output control in the first sealing mode or perform the output control in the second sealing mode. In the present modification, two operational buttons or the like which are energy operation input sections are provided, and if an operation input is performed with one of the operational buttons, the processor 21 the output controller 26) performs the output control of the electric energy the first sealing mode, and the energy treatment instrument 2 is actuated in the first mode (first actuation mode) to coagulate the treated target (blood vessel). Then, when an operation input is performed with the other of the operational buttons, the processor 21 performs the output control of the electric energy in the second sealing mode in which the performance of sealing the blood vessel by the treatment energy is higher than that in the first sealing mode. Accordingly, the energy treatment instrument 2 coagulates the treated target (blood vessel), and is actuated in the second mode (second actuation mode) in which the state of the application of the treatment energy to the treated target (blood vessel) is different from that in the first mode, and the coagulation performance (sealing performance) of the treated target (blood vessel) by the treatment energy is higher in the second mode than in the first mode. In the present modification, a notification section (not shown) which shows a judgement result of whether or not the oxygen concentration X is higher than the oxygen concentration threshold Xth1 or whether the grasped blood vessel is a blood vessel of the circulatory system or a blood vessel of the pulmonary circulation is provided in, for example, the controller 3. In a certain example, the notification section is an LED, and lights when it is set that the grasped blood vessel is a blood vessel of the pulmonary circulation (regarding the artery, when it is judged that the oxygen concentration X is less than or equal to the oxygen concentration threshold Xth1). In another example, the notification section may be a buzzer, a display screen, or the like.

In another certain modification, the notification section is a display screen or the like, and may notify of the detection result of the parameter regarding the kind of grasped blood vessel in the detector 41, or the oxygen concentration X calculated in the processor 21. In the present modification, the surgeon judges whether or not the oxygen concentration X is higher than the oxygen concentration threshold Xth1, on the basis of information provided by the notification section. Then the surgeon judges whether the blood vessel is a blood vessel of the circulatory system or a blood vessel of the pulmonary circulation. Then the surgeon judges which of the two operational buttons is used to perform an operation input, and selects whether to cause the processor 21 to perform. the output control in the first sealing mode or perform the output control in the second sealing mode.

Note, that in another certain modification, wall thickness T of the blood vessel may be used instead of the oxygen concentration X of the blood vessel. In this case, an angle sensor (not shown) is provided as the detector 41 in the end effector 7 or separately from the energy treatment instrument 2. The angle sensor detects the angle between the first grasping piece 15 and the second grasping piece 16 in a state where a treated target such as the blood vessel N is grasped between the grasping pieces 15 and 16. In this instance, the angle detected by the angle sensor is detected as the parameter regarding the kind of grasped blood vessel M. Then the processor 21 calculates the wall thickness T of the grasped blood vessel on the basis of the detection result in the detector 41 in this instance, for example, a table or the like indicating the relation between the angle between the first grasping piece 15 and the second grasping piece 16 detected by the angle sensor and the wall thickness T the grasped blood vessel is stored in the storage medium 22. Then the processor 21 calculates the wall thickness T of the grasped blood vessel on the basis of the table indicating the relation between the angle between the first grasping piece 15 and the second grasping piece 16 detected by the angle sensor and the wall thickness T of the grasped blood vessel.

In the present modification, the angle between the first grasping piece 15 and the second grasping piece 16 is acquired in step S101, and the wall thickness T of the grasped blood vessel is calculated in step S102. In step S104, whether or not the wall thickness T is greater than a wall thickness threshold Tth is judged. Here, it is assumed that the blood vessel of the pulmonary circulation is smaller in the wall thickness T of the blood vessel than the blood vessel of the circulatory system having the same diameter. Thus, when the wall thickness T is greater than the wall thickness threshold Tth (step S104—Yes), it is set that the grasped blood vessel is a blood vessel of the circulatory system (step S105). When the wall thickness T is less than or equal to the wall thickness threshold Tth (step S104—No), it is set that the grasped blood vessel is a blood vessel of the pulmonary circulation (step S107).

Note that the treatment system 1 according to the present embodiment can also be used in a sealing treatment of a vein. When the sealing treatment of the vein is conducted, an electric signal indicating that the sealing treatment of the vein is conducted is acquired in addition to the detection result in the detector 41, for example, in the processing in step S101. The electric signal indicating that the sealing treatment of the vein is conducted is acquired, for example, when an operation input is performed with an operational button or the like provided separately from the energy operation input section. Further, in step S104, whether or not the oxygen concentration X is lower than an oxygen concentration threshold Xth2 is judged. The oxygen concentration threshold Xth2 is stored, for example, in the storage medium 22. As described above, veins are lower in the oxygen concentration X in the circulatory system than in the pulmonary circulation. Thus, when the oxygen concentration X is lower than the oxygen concentration threshold Xth2 (step S104—Yes), it is set that the grasped blood vessel is a blood vessel of the circulatory system (step S105). When the oxygen concentration X is equal to or more than the oxygen concentration threshold Xth2 (step S104—No), it is set that the grasper blood vessel is a blood vessel of the pulmonary circulation (step S107).

Second Embodiment

Next, a second embodiment of the present invention is described with reference to FIG. 12 to FIG. 14. The second embodiment is a modification in which the configuration according to the first embodiment is modified as below. Note that the same parts as those in the first embodiment are denoted with the same reference signs and are not described.

FIG. 12 is a diagram showing a control configuration in the treatment system 1 according to the present embodiment. As shown in FIG. 12, in the present embodiment, a grasping force adjustment element 51 is provided in the energy treatment instrument 2. The force of grasping the treated target (blood vessel) between the grasping pieces 15 and 16 changes in accordance with the driving state of the grasping force adjustment element 51. That is, the force of grasping the treated target between the grasping pieces 15 and 16 is adjusted by the grasping force adjustment element 51. Moreover, in the present embodiment, a driving electric power output source 52 is provided in the controller 3. The driving electric power output source 52 is electrically connected to the grasping force adjustment element 51 via an electricity supply path 53 extending through the cable 10. Here, the driving electric power output source 52 may be integral with the aforementioned energy output sources 32 and 47 or the like, or may be formed separately from the energy output sources 32 and 47 or the like.

The driving electric power output source 52 comprises a conversion circuit, an amplifier circuit, and others, and converts electric power from the power source 31 into driving electric power for the grasping force adjustment element 51. Then the driving electric power output source 52 outputs the driving electric power resulting from the conversion, and the output driving electric power is supplied to the grasping force adjustment element 51 through the electricity supply path 53. The processor 21 controls driving of the driving electric power output source 52, and controls the output of the driving electric power from the driving electric power output source 52. Thereby, the supply of the driving electric power to the grasping force adjustment element 51 is controlled, and the driving of the grasping force adjustment element 51 is controlled. In the present embodiment, the actuation state of the energy treatment instrument 2 is switched between the first mode (first actuation mode) and the second mode (second actuation mode) in accordance with the driving state of the grasping force adjustment element 51. In the present embodiment, the force of grasping the treated target (blood vessel) between the grasping pieces 15 and 16 varies between the first mode and the second mode.

Figure 13:
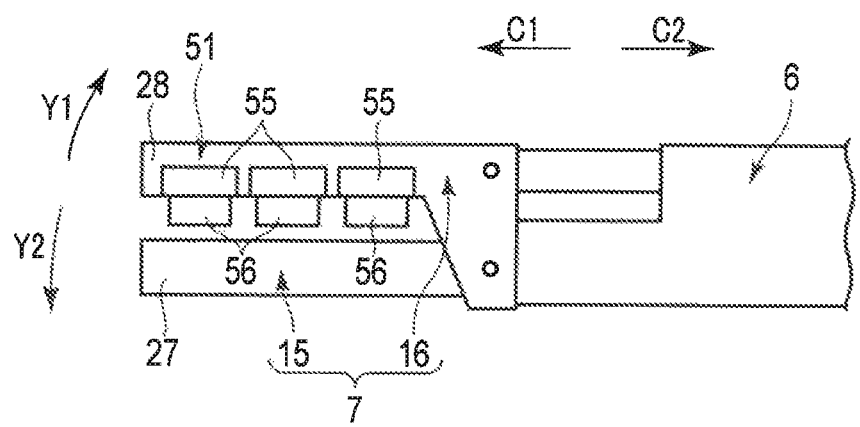
FIG. 13 is a schematic diagram showing one example of a grasping force adjustment element according to the second embodiment.
Figure 14:
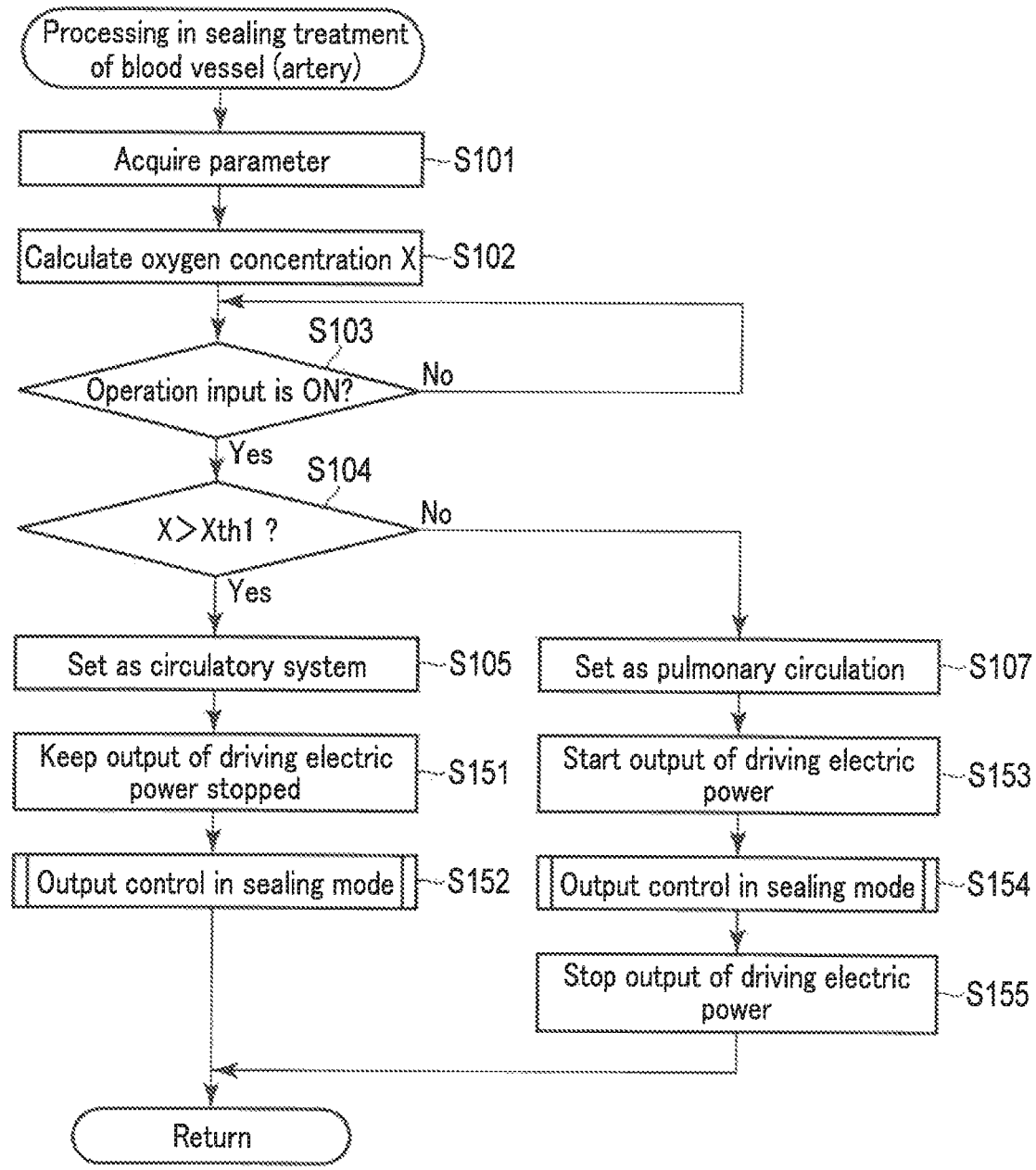
FIG. 14 is a flowchart showing processing at the processor in a sealing treatment of the blood vessel using the treatment system according to the second embodiment.

FIG. 13 is a diagram showing one example of the grasping force adjustment element 51. In the example shown in FIG. 13, a heater 55 and a volume changing portion 56 are provided as the grasping force adjustment element 51 in the second grasping piece 16. The volume changing portion 56 is made of an electrically insulating material such as parylene, nylon, or ceramics, and can abut on the first grasping piece 15 (the first electrode 27) by the closing of the grasping pieces 15 and 16. In a state where the volume changing portion 56 is in abutment with the first grasping piece 15, the electrodes 27 and 28 are apart from each other, and the contact between the electrodes 27 and 28 is prevented by the volume changing portion 56, Moreover, the volume changing portion 56 is made of a material having a high thermal expansion coefficient.

The driving electric power is output to the heater 55 from the driving electric power output source 52, whereby the grasping force adjustment element 51 is driven, and heat is generated in the heater 55. Due to the heat generated in the heater 55, the temperature of the volume changing portion 56 rises, and the volume changing portion 56 expands (the volume of the volume changing portion 56 increases.). By the expansion of the volume changing portion 56 in a state where the blood vessel (treated target) is grasped between the grasping pieces 15 and 16, the distance between the grasping pieces 15 and 16 decreases, and the force of grasping the treated target between the grasping pieces 15 and 16 increases. Note that in the present example, the coagulation and cutting or the like of the treated target are not performed by the heat generated in the heater 55.

Furthermore, in another certain example, a Peltier element may be provided instead of the heater 55. In this case, the driving electric power is output to the Peltier element from the driving electric power output source 52, and the Peltier element thereby moves the heat to the side of the volume changing portion 56. Due to the movement of the heat by the Peltier element, the temperature of the volume changing portion 56 rises, and the volume changing portion 56 expands. Thus, in a state where the blood vessel (treated target) is grasped between the grasping pieces 15 and 16, the distance between the grasping pieces 15 and 16 decreases, and the force of grasping the treated target between the grasping pieces 15 and 16 increases, as described above.

New, functions and advantageous effects according to the present embodiment are described. FIG. 14 is a flowchart showing processing at the processor 21 in a sealing treatment of the blood vessel (artery) using the treatment system 1 according to the present embodiment. In the present embodiment as well as in the embodiment and others described above, the processor 21 performs the processing shown in steps S101 to S104 in the sealing treatment of the blood vessel. Further, when the oxygen. concentration X is higher than the oxygen concentration threshold Xth1 (step S104—Yes), the setting section 25 sets that the grasped blood vessel is a blood vessel of the circulatory system (step S105). Then the processor 21 keeps the output of the driving electric power to the grasping force adjustment element 51 from the driving electric power output source 52 stopped (step S151). Thus, the grasping force adjustment element 51 is not driven, and the volume changing portion 56 does not expand. Therefore, the force of grasping the treated target between the grasping pieces 15 and 16 is maintained. Then the processor 21 performs the output control of the electric energy from the energy output source 32 or the like in the sealing mode (step S152). In the output control in the sealing mode, the processor 21 performs, for example, processing similar to that in the output control in the first sealing mode according to the first embodiment (see FIG. 6). In a state where the output of the driving electric power to the grasping force adjustment element 51 from the driving electric power output source 52 is stopped by the processor 21 and the grasping force adjustment element 51 is not driven, the energy treatment instrument 2 is actuated in the first mode (first actuation mode) to coagulate the grasped treated target (blood vessel).

On the other hand, when the oxygen concentration X is less than or equal to the oxygen concentration threshold Xth1 (step S104—No), the setting section 25 sets that the grasped blood vessel is a blood vessel of the pulmonary circulation (step S107). Then the processor 21 starts the output of the driving electric power to the grasping force adjustment element 51 from the driving electric power output source 52 (step S153). Thus, the grasping force adjustment element 51 is driven, and the volume changing portion 56 expands. Therefore, the force of grasping the treated target between the grasping pieces 15 and 16 increases. Then the processor 21 performs the output control of the electric energy from the energy output source 32 or the like in the sealing mode (step S154). In the output control in the sealing mode, the processor 21 performs, for example, processing similar to that in the output control in the first sealing mode according to the first embodiment (see FIG. 6). After finishing the output control in the sealing mode, the processor 21 stops the output of the driving electric power to the creeping force adjustment element 51 from the driving electric power output source 52 (step S155). In a state where the driving electric power is output to the grasping force adjustment element 51 from the driving electric power output source 52 by the processor 21 and the grasping force adjustment element 51 is driven, the energy treatment instrument 2 coagulates the grasped treated target. (blood vessel), and is actuated in the second mode (second actuation mode) different from the first mode. As described above, in the present embodiment, the processor 21 switches the actuation state of the energy treatment instrument 2 between the first mode (first actuation mode) and the second mode (second actuation mode) by controlling the output of the driving electric power from the driving electric power output source 52 on the basis of the setting of the kind of grasped blood vessel. In the energy treatment instrument 2, the driving state of the grasping force adjustment element 51 varies between the first mode and the second mode, so that the force of grasping the treated target (blood vessel) between the grasping pieces 15 and 16 varies between the first mode and the second mode.

The control by the processor 21 is performed as described above, whereby in the present modification, the processor 21 makes the force of grasping the blood vessel (treated target)

between the grasping pieces 15 and 16 greater when it is set that the grasped blood vessel is a blood vessel of the pulmonary circulation than when it is set that the grasped blood vessel is a blood vessel of the circulatory system. That is, in the energy treatment instrument 2, the force of grasping the treated target (blood vessel) between the grasping pieces 15 and 16 is greater in the second mode (second actuation mode) than in the first mode (first actuation mode). Thus, even if the grasped blood vessel is a blood vessel of the pulmonary circulation, the force of grasping the blood vessel between the grasping pieces 15 and 16 is increased, so that the grasped blood vessel is properly sealed. That is, in accordance with the kind of blood vessel, the blood vessel is properly sealed by use of the treatment energy, and suitable treatment performance (sealing performance) is achieved. Therefore, suitable treatment performance is achieved regardless of the kind of blood vessel.

Modification of Second Embodiment

Note that the grasping force adjustment element 51 is not limited to the configuration described above. For example, in a certain modification, an electric motor and an abutment member are provided as the grasping force adjustment element 51. In this case, the handle 12 is closed relative to the grip 11, and the handle 12 thereby abuts on the abutment member, and the handle 12 closes relative to the grip 11 until abutting on the abutment member. Then the processor 21 (the output controller 26) controls the output of the driving electric power to the electric motor from the driving electric power output source 52, and controls the driving of the electric motor. Due to the driving of the electric motor, the abutment. member moves, and the position of the abutment member changes. Accordingly, the stroke of the handle at the time of the closing of the handle 12 relative to the trip 11 changes. In the present modification, the processor 21 adjusts the position of the abutment member on the basis of the oxygen concentration X, thereby making the stroke of the handle 12 at the time of its closing greater when it is set that the grasped blood vessel is a blood vessel of the pulmonary circulation than when it is set that the grasped blood vessel is a blood vessel of the circulatory system. Consequently, in the present modification as well, the force of grasping the blood vessel (treated target) between the grasping pieces 15 and 16 is greater when the grasped blood vessel is a blood vessel of the pulmonary circulation (the second mode of the energy treatment instrument 2) than when the grasped blood vessel is a blood vessel of the circulatory system (the first mode of the energy treatment instrument 2).

Furthermore, according to the configuration in which one of the grasping pieces 15 and 16 is formed by the rod member that is inserted through the sheath 6, a support member which supports the rod member on the most distal side inside the sheath 6, and the electric motor or the like which is driven and thereby moves the support member are provided as the grasping force adjustment element 51. In this case, the electric motor or the like is driven in accordance with the set kind of blood vessel, and thereby the position at which the rod member is supported by the support member is changed. Accordingly, in a state where the treated target (blood vessel) is grasped between the grasping pieces 15 and 16, the bending amount of a distal portion of the rod member (one of the grasping pieces 15 and 16) changes, and the grasping force between the grasping pieces 15 and 16 changes. Moreover, the control to adjust the grasping force as in the second embodiment is suitably applicable if the grasping force adjustment element 51 which changes the force of grasping the treated target (blood vessel) between the grasping pieces 15 and 16 is provided.

Furthermore, in another certain modification, an operational button or the like may be provided as a driving operation input section which outputs driving electric power from the driving electric power output source 52. In the present modification, the surgeon or the like judges whether or not to output the driving electric power. Moreover, in the present modification, the aforementioned notification section is provided in, for example, the controller 3. When it is notified that the oxygen concentration X is higher than the oxygen concentration threshold Xth1 or it is judged that the grasped blood vessel is a blood vessel of the circulatory system, the surgeon does not perform an operation input with the operational button (driving operation input section). Thus, no driving electric power is output to the grasping force adjustment element 51 (the heater 55) from the driving electric power output source 52, and the volume changing portion 56 does not expand. Accordingly, the energy treatment instrument 2 is actuated in the first mode (first actuation mode). On the other hand, when it is notified that the oxygen concentration X is less than or equal to the oxygen concentration threshold Xth1 or it is judged that the grasped blood vessel is a blood vessel of the pulmonary circulation, the surgeon performs an operation input with the operational button 18. Thus, the driving electric power is output to the grasping force adjustment element 51 (the heater 55) from the driving electric power output source 52, and the volume changing portion 56 expands due to the heat generated in the heater 55. Accordingly, the energy treatment instrument 2 is actuated in the second mode (second actuation mode), and the force of grasping the treated target between the grasping pieces 15 and 16 increases.

Other Modifications

Note that in a certain modification, one of the first embodiment and its modifications and one of the second embodiment and its modifications may be combined. In this case, when the oxygen concentration X is higher than the oxygen concentration threshold Xth1, the processor 21 sets that the grasped blood vessel is a blood vessel of the circulatory system, and performs the output control of the electric energy from the energy output sources 32 and 47 or the like in the first sealing mode, thereby applying the treatment energy to the blood vessel. Further, when the oxygen concentration X is less than or equal to the oxygen concentration threshold Xth1, the processor 21 sets that the grasped blood vessel is a blood vessel of the pulmonary circulation, and performs the output control of the electric energy from the energy output sources 32 and 47 or the like in the second sealing mode in which the performance of sealing the blood vessel by the treatment energy is higher than that in the first sealing mode, thereby applying the treatment energy to the blood vessel. That is, in the present modification as well as in the first embodiment, the performance of sealing the blood vessel by the treatment energy is higher in the second sealing mode of the energy treatment instrument 2 than in the first sealing mode. Moreover, in the present modification, the processor 21 makes the force of grasping the treated target between the grasping pieces 15 and 16 greater when the oxygen concentration X is less than or equal to the oxygen concentration threshold Xth1 (the second mode of the energy treatment instrument 2) than when the oxygen concentration X is higher than the oxygen concentration threshold Xth1 (the first mode of the energy treatment instrument 2).

In the embodiments and others described above, the energy treatment instrument (2) of the treatment system (1) comprises the first grasping piece (15), and the second grasping piece (16) which opens or closes relative to the first grasping piece (15) and which grasps a blood vessel between the first grasping piece (15) and the second grasping piece (16). Further, in accordance with the kind of grasped blood vessel, the actuation state of the energy treatment instrument (2) is switched between the first mode to coagulate the blood vessel of the circulatory system, and the second mode to coagulate the blood vessel of the pulmonary circulation in contrast to the first mode. Further, in the treatment system (1), the energy output source (32; 47; 32, 47) outputs electric energy which is supplied to the energy treatment instrument (2), and the electric energy is supplied to the energy treatment instrument (2), whereby the treatment energy is applied to the blood vessel grasped between the first grasping piece (15) and the second grasping piece (16). The processor (21) sets whether the blood vessel is a blood vessel of the circulatory system or a blood vessel of the pulmonary circulation. The processor (21) performs at least one of the following: controlling the output of the electric energy from the energy output source (32; 47; 32, 47) in accordance with the setting c the kind of blood vessel, and making the force of grasping the treated target between the first grasping piece (15) and the second grasping piece (16) greater when it is set that the blood vessel is a blood vessel of the pulmonary circulation than when it is set that the blood vessel is a blood vessel of the circulatory system.

Characteristic matters are additionally noted below.

(Additional Note 1)

A treatment method comprising:

closing a first grasping piece and a second grasping piece relative to each other, and grasping a blood vessel between the first grasping piece and the second grasping piece;

supplying electric energy to an energy treatment instrument from an energy output source, and applying treatment energy to the blood vessel grasped between the first grasping piece and the second grasping piece;

setting whether the grasped blood vessel is a blood vessel of a circulatory system or a blood vessel of a pulmonary circulation; and performing at least one of the following: controlling the output of the electric energy from the energy output source on the basis of the setting of the kind of grasped blood vessel, and making the force of grasping the blood vessel between the first grasping piece and the second grasping piece greater when it is set that the grasped blood vessel is a blood vessel of the pulmonary circulation than when it is set that the grasped blood vessel a blood vessel of the circulatory system.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended clams and their equivalents.

What is claimed is:

1. A treatment system comprising:
an energy treatment instrument including a first grasping piece, and a second grasping piece which grasps a blood vessel between the first grasping piece and the second grasping piece;
an energy output source configured to output electric energy that is supplied to the energy treatment instrument, and apply treatment energy to the blood vessel grasped between the first grasping piece and the second grasping piece by supplying the electric energy to the energy treatment instrument; and
a processor configured to determine whether the grasped blood vessel is a blood vessel of a systemic circulatory system or a blood vessel of a pulmonary system based on oxygen concentration or thickness of a wall of the blood vessel, wherein:
when the processor determines that the grasped blood vessel is from the systemic circulatory system, the processor configured to switch an actuation state of the energy treatment instrument to a first mode to coagulate the blood vessel of the systemic circulatory system at a first output setting; and
when the processor determines that the grasped blood vessel is from the pulmonary system, the processor is configured to switch the actuation state of the energy treatment instrument to a second mode to coagulate the blood vessel of the pulmonary system at a second output setting, the first output setting being at a first electric energy output and the second output setting being at a second electric energy output;
in the first mode, the first electric energy output is performed, and when an impedance of the blood vessel reaches an impedance threshold, the first electric energy output is stopped;
in the second mode, the second electric energy output lower than the first electric energy output is performed, and when an impedance of the blood vessel reaches the impedance threshold, the second electric energy output is stopped;
an increase rate of the impedance of the blood vessel in the second mode is lower than in the first mode; and
a time for the impedance of the blood vessel to reach the impedance threshold in the second mode is longer than in the first mode.

2. The treatment system according to claim 1, wherein when it is set that the blood vessel is a blood vessel of the pulmonary system, the processor causes the electric energy to be intermittently output more than one time by stopping the output of the electric energy after starting the output of the electric energy, and again starting the output of the electric energy after once stopping the output of the electric energy.

3. The treatment system according to claim 1, wherein the processor is configured to detect the impedance between the first grasping piece and the second grasping piece.

4. The treatment system according to claim 1, further comprising a detector which detects a parameter regarding the grasped blood vessel between the first grasping piece and the second grasping piece,
wherein the processor is configured to set whether the blood vessel is a blood vessel of the systemic circulatory system or a blood vessel of the pulmonary system based on a detection result in the detector.

5. The treatment system according to claim 1, wherein the first grasping piece includes a first electrode, the second grasping piece includes a second electrode, and the energy output source passes a high-frequency current as the treatment energy through the blood vessel between the first grasping piece and the second grasping piece by supplying the output electric energy to the first electrode and the second electrode.

6. A controller which is used together with an energy treatment instrument, the energy treatment instrument including a first grasping piece, and a second grasping piece which opens or closes relative to the first grasping piece and which grasps a blood vessel between the first grasping piece and the second grasping piece, the controller comprising:

an energy output source configured to output electric energy that is supplied to the energy treatment instrument, and which applies treatment energy to the blood vessel grasped between the first grasping piece and the second grasping piece by the supply of the electric energy to the energy treatment instrument; and a processor configured to determine whether the grasped blood vessel is a blood vessel of a systemic circulatory system or a blood vessel of a pulmonary system based on oxygen concentration or thickness of a wall of the blood vessel, wherein:

when the processor determines that the grasped blood vessel is from the systemic circulatory system, the processor configured to switch an actuation state of the energy treatment instrument to a first mode to coagulate the blood vessel of the systemic circulatory system at a first output setting; and when the processor determines that the grasped blood vessel is from the pulmonary system, the processor is configured to switch the actuation state of the energy treatment instrument to a second mode to coagulate the blood vessel of the pulmonary system at a second output setting, the first output setting being at a first electric energy output and the second output setting being at a second electric energy output;

in the first mode, the first electric energy output is performed, and when an impedance of the blood vessel reaches an impedance threshold, the first electric energy output is stopped;

in the second mode, the second electric energy output lower than the first electric energy output is performed, and when an impedance of the blood vessel reaches the impedance threshold, the second electric energy output is stopped;

an increase rate of the impedance of the blood vessel in the second mode is lower than in the first mode; and a time for the impedance of the blood vessel to reach the impedance threshold in the second mode is longer than in the first mode.

* * * * *